US005731284A

United States Patent [19]
Williams

[11] Patent Number: 5,731,284
[45] Date of Patent: Mar. 24, 1998

[54] METHOD FOR TREATING ALZHEIMER'S DISEASE USING GLIAL LINE-DERIVED NEUROTROPHIC FACTOR (GDNF) PROTEIN PRODUCT

[75] Inventor: Lawrence R. Williams, Thousand Oaks, Calif.

[73] Assignee: Amgen Inc., Thousand Oaks, Calif.

[21] Appl. No.: 535,682

[22] Filed: Sep. 28, 1995

[51] Int. Cl.$^6$ .............................. A61F 2/00; A61K 47/00; A61K 31/685; A61K 38/00
[52] U.S. Cl. ........................................ 514/8; 514/21
[58] Field of Search ................................. 514/8, 21

[56] References Cited

U.S. PATENT DOCUMENTS

| | | | |
|---|---|---|---|
| 4,518,584 | 5/1985 | Mark et al. | 424/85 |
| 4,892,538 | 1/1990 | Aebischer et al. | 604/891.1 |
| 5,011,472 | 4/1991 | Aebischer et al. | 604/50 |
| 5,106,627 | 4/1992 | Aebischer et al. | 424/424 |
| 5,252,714 | 10/1993 | Harris et al. | 530/391.9 |
| 5,639,275 | 6/1997 | Baelge et al. | 604/891.1 |
| 5,641,749 | 6/1997 | Yan et al. | 514/12 |
| 5,641,750 | 6/1997 | Louis | 514/12 |

FOREIGN PATENT DOCUMENTS

| | | |
|---|---|---|
| 154 316 | 3/1985 | European Pat. Off. |
| 401 384 | 12/1989 | European Pat. Off. |
| 423 980 | 10/1990 | European Pat. Off. |
| WO 91/10425 | 7/1991 | WIPO |
| WO 91/10470 | 7/1991 | WIPO |
| 9306116 | 1/1993 | WIPO |
| WO 93/06116 | 4/1993 | WIPO |

OTHER PUBLICATIONS

Varon et al., (1979) *Ann. Rev. Neurosci.*, 1:327–361.
Thoenen et al., (1985) *Science*, 229:238–242.
Thoenen et al., (1991) *Trends Neurosci.*, 14:165–170.
Lapchak et al., (1993) *Rev. Neurosci.*, 3:1–10.
Bothwell, (1995) *Ann. Rev. Neurosci.*, 18:223–253.
Chao, (1995) *TINS*, 18:321–326.
Venero et al., (1993) *Neuroreport* 4:959–962.
Hefti, (1994) *J. Neurobiol.* 25:1418–1435.
Olson, (1994) *Neurochem. Jul.* 15:1–3.
Batchelor et al., (1989) *J. Comp. Neurol.* 284:187–204.
Kiss et al., (1988) *Neurosci.* 27:731–748.
Woolf et al., (1989) *Neurosci.* 30:143–152.
Lin et al., (1993) *Science* 260:1130–1132.
Krieglstein et al., (1995) *EMBO J.* 14:736–742.
Poulsen et al., (1994) *Neuron* 13:1245–1252.
Hudson et al., (1995) *Brain Res. Bull.* 36:425–432.
Beck et al., (1995) *Nature* 373:339–341.
Tomac et al., (1995) *Nature* 373:335–339.
Hoffer et al., (1994) *Neurosci. Lett.* 182:107–111.
Oppenheim et al., (1995) *Nature* 373:344–346.
Zurn et al., (1994) *Neuroreport* 6:113–118.
Yan et al., (1995) *Nature* 373:341–344.
Henderson et al., (1994) *Science* 266:1062–1064.

Miller et al., (1994) *Soc. Neurosci. Abstr.* 20:1300.
Selkoe, (1991) *Neuron.* 6:487–498.
Gage et al., (1986) *Neurosci.* 19:241–255.
Hagg et al., (1989) *Brain Res.* 505:29–38.
Hefti, (1986) *J. Neurosci.* 6:2155–2162.
Springer et al., (1987) *J. Neurosci. Res.* 17:111–118.
Sofroniew et al., (1993) *J. Neurosci.* 13:5263–5276.
Knusel et al., (1992) *J. Neurosci.* 12:4391–4402.
Koliatsos et al., (1994) *J. Comp. Neurol.* 343:247–262.
Koliatsos et al., (1991) *Ann. Neurol.* 30:831–840.
Morse et al., (1993) *J. Neurosci.* 13:4146–4156.
Venero et al., (1994) *Neurosci.* 59:797–815.
Widmer et al., (1993) *Neuroreport* 4:363–366.
Williams et al., (1989) *Brain Res.* 498:243–256.
Williams et al., (1986) *Proc. Natl. Acad. Sci. USA* 83:9231–9235.
Phelps et al., (1989) *Neurobiol. Aging* 10:205–207.
Olson, (1994) *Neurochem. Jul.* 25:1–3.
Olson et al., (1992) *J. Neural Transm.* 4:79–95.
Petty et al., (1994) *Ann. Aug.* 36:244–246.
Hagg et al., (1989) *Neurosci.* 30:95–103.
Rylett et al., (1993) *J. Neurosci.* 13:3956–3963.
Lapchak, (1993) *Exp. Neurol.* 124:16–20.
Butcher et al., (1989) *Neurobiol. Aging* 10:557–570.
Woolf et al., (1994) *Neurosci. Sep.* 62:327–331.
Della Seta er al., (1994) *Pharmacol.* 49:701–705.
Lewin et al., (1993) *Trends Neurosci. Sep.* 16:353–359.
Williams et al. (1991) *Exp. Neurol.* 113:31–37.
Hefti et al., (1993) *Adv. Pharmacol.* 24:239–273.
Fischer et al., (1994) *Proc. Natl. Acad. Sci. USA* 91:8607–8611.
Schmidt–Kastner et al., (1994) *Mol. Brain Res.* 26:325–330.
Schaar et al., (1993) *Exp. Neurol.* 124:368–371.
Schaar et al., (1994) *Exp. Neurol.* 130:387–393.
Dayhoff, (1972) *Atlas of Protein Sequence and Structure* 5:124.
Cunningham et al., (1989) *Science* 244:1081–1085.
Malik et al., (1992) *Exp. Hematol.* 20:1028–1035.
Francis, (1992) *Focus on Growth Factors* 3(2):4–10.
Chamow et al., (1994) *Bioconjugate Chem.* 5:133–140.
Winn et al., (1991) *Exper. Neurol.* 113:322–329.
Aebischer et al., (1991) *Exper. Neurol.* 111:269–275.
Tresco et al., (1992) *ASAIO* 38:17–23.
Kearns et al., (1995) *Brain Res.*, 672:104–111.
Stromberg et al., (1995) *Exp. Neurol.* 124:401–412.
Schrier et al., (1967) *Neurochem.* 14:977–985.
Smolen, Ed. Conn, (1990) *Neurosciences* 3:208–229.
Emmett et al., (1995) *Brain Res.* 673:199–207.
Alderson, (1995) *Eur. J. Neurosci.*

*Primary Examiner*—Cecilia J. Tsang
*Assistant Examiner*—P. Lynn Touzeau
*Attorney, Agent, or Firm*—Daniel R. Curry; Ron K. Levy; Steven M. Odre

[57] ABSTRACT

The present invention relates generally to methods for treating injury or degeneration of basal forebrain cholinergic neurons by administering glial cell line-derived neurotrophic factor (GDNF). The invention relates specifically to methods for treating Alzheimer's disease.

11 Claims, 7 Drawing Sheets

METHOD FOR TREATING ALZHEIMER'S DISEASE USING GLIAL LINE-DERIVED NEUROTROPHIC FACTOR (GDNF) PROTEIN PRODUCT

BACKGROUND OF THE INVENTION

The present invention relates generally to methods for treating injury or degeneration of basal forebrain cholinergic neurons by administering glial cell line-derived neurotrophic factor (GDNF) protein product. The invention relates specifically to methods for treating Alzheimer's disease.

Neurotrophic factors are natural proteins, found in the nervous system or in non-nerve tissues innervated by the nervous system, that function to promote the survival and maintain the phenotypic differentiation of nerve and/or glial cells (Varon et al., Ann. Rev. Neuroscience, 1:327, 1979; Thoenen et al., Science, 229:238, 1985). Because of this physiological role, neurotrophic factors are useful in treating the degeneration of nerve cells and loss of differentiated function that results from nerve damage. Nerve damage is caused by conditions that compromise the survival and/or proper function of one or more types of nerve cells, including: (1) physical injury, which causes the degeneration of the axonal processes and/or nerve cell bodies near the site of injury, (2) temporary or permanent cessation of blood flow (ischemia) to parts of the nervous system, as in stroke, (3) intentional or accidental exposure to neurotoxins, such as the cancer and AIDS chemotherapeutic agents cisplatinum and dideoxycytidine (ddC), respectively, (4) chronic metabolic diseases, such as diabetes or renal dysfunction, or (5) neurodegenerative diseases such as Parkinson's disease, Alzheimer's disease, and Amyotrophic Lateral Sclerosis (ALS), which result from the degeneration of specific neuronal populations. In order for a particular neurotrophic factor to be potentially useful in treating nerve damage, the class or classes of damaged nerve cells must be responsive to the factor; different neurotrophic factors typically affect distinctly different classes of nerve cells.

The fast neurotrophic factor to be identified was nerve growth factor (NGF). NGF is the first member of a defined family of trophic factors, called the neurotrophins, that currently includes brain-derived neurotrophic factor (BDNF), neurotrophin-3 (NT-3), NT-4/5, and NT-6 (Thoenen, Trends. Neurosci. 14:165–170, 1991; Lapchak et at., Rev. Neurosci., 3:1–10, 1993; Bothwell, Ann. Rev. Neurosci., 18:223–253, 1995). These neurotrophins are known to act via the family of trk tyrosine kinase receptors, i.e., trkA, trkB, trkC, and the low affinity p75 receptor (Lapchak et al., Rev. Neurosci. 3:1–10, 1993; Bothwell, Ann. Rev. Neurosci., 18:223–253, 1995; Chao et al., TINS 18:321–326, 1995). In the central nervous system (CNS), the expression of trkA, the receptor for NGF, is almost exclusively limited to the cholinergic neurons in the basal forebrain (Venero et al., Neuroreport 4:959–962, 1993), which also express p75 and trkB. These cholinergic neurons are of particular neurologic interest, because cholinergic neuronal degeneration and/or dystrophy is a hallmark of Alzheimer's disease (Hefti, J. Neurobiol. 25:1418–1435, 1994; Olson, Neurochem. Jul. 15:1–3, 1994). The basal forebrain cholinergic neurons can be readily identified in morphologic preparations using acetylcholinesterase histochemistry or with immunohistochemistry using antibody to choline acetyltransferase (ChAT), the synthetic enzyme for acetylcholine, or to p75 (Batchelor et al., J. Comp. Neurol. 284:187–204, 1989; Kiss et al., Neurosci. 27:731–748, 1988; Woolf et al., Neurosci. 30:143–152, 1989).

Glial cell line-derived neurotrophic factor (GDNF) is a recently discovered protein identified and purified using assays based upon its efficacy in promoting the survival and stimulating the transmitter phenotype of mesencephalic dopaminergic neurons in vitro (Lin et al., Science 260:1130–1132, 1993). GDNF is a glycosylated disulfide-bonded homodimer that has its closest structural homology to the transforming growth factor (TGF) superfamily of neurotrophic proteins (Lin et al., Science 260:1130–1132, 1993; Krieglstein et al., EMBO J. 14:736–742, 1995; Poulsen et al., Neuron 13:1245–1252, 1994). In vivo, treatment with exogenous GDNF stimulates the dopaminergic phenotype of substantia nigra neurons, and restores functional deficits induced by axotomy or dopaminergic neurotoxins in animal models of Parkinson's disease (Hudson et al., Brain Res. Bull. 36:425–432; 1995; Beck et al., Nature 373:339–341, 1995; Tomac et al., Nature 373:335–339, 1995; Hoffer et al., Neurosci. Lett. 182:107–111, 1994). Although originally thought to be relatively specific for dopaminergic neurons, at least in vitro, subsequent experiments have found that GDNF has neurotrophic efficacy on brain stem and spinal cord cholinergic motor neurons, both in vivo and in vitro (Oppenheim et al., Nature 373:344–346, 1995; Zurn et al., Neuroreport 6:113–118, 1994; Yan et al., Nature 373:341–344, 1995; Henderson et al., Science 266:1062–1064, 1994). Evidence is beginning to emerge indicating that GDNF may have a larger spectrum of neurotrophic targets besides mesencephalic dopaminergic and somatic motor neurons (Yan and Matheson, Nature 373:341–344, 1995; Miller et al., Soc. Neurosci. Abstr. 20:1300, 1994).

Alzheimer's disease is a progressive dementia characterized by failure of recent memory, amnesia, disturbances in emotional behavior, and difficulty in managing spatial relationships or motor skills. The disease occurs throughout the world and accounts for one-half to two-thirds of all cases of late-life intellectual failure in many developed countries having populations with high life expectancies. (Selkoe, Neuron, 6:487–498, 1991.)

Alzheimer's disease is diagnosed mainly by clinical symptoms, after other causes of dementia have been excluded. After death, the diagnosis can be conclusively established by the observation of numerous characteristic neurofibrillary tangles and senile plaques in the brain that accompany the cerebral degeneration seen in Alzheimer's disease. Neurofibrillary tangles are abnormal tangles of twisted fibers inside degenerating nerve cell bodies and neurites. The principal structures in these fibrous deposits are pairs of about 10 nm twisted filaments, referred to as paired helical filaments (PHFs). These PHFs appear to be composed mainly of insoluble aggregates of modified tau proteins. (Selkoe, Neuron, 6:487–498, 1991.)

The classic senile plaque of Alzheimer's disease is a complex lesion containing several abnormal elements: a core central deposit of extracellular amyloid fibrils, surrounded by dystrophic nerve cells, activated microglia, and fibrillary astrocytes. These plaques occur abundantly in three conditions: Alzheimer's disease, trisomy 21, and, to a lesser extent, normal brain aging. The amyloid fibrils of the plaque core are ultrastructurally distinct from PHFs, being extracellular, unpaired, and about 8 nm in diameter, but they closely resemble the amyloid filaments that accumulate in nonneural tissues in a variety of unrelated systemic amyloidoses. Amyloid deposits also occur in the walls of some or many cerebral and leptomeningeal blood vessels in Alzheimer's disease. The subunit composition of amyloid filaments is a peptide called the amyloid β-protein (AβP). The AβP peptide is a proteolytic fragment of a larger 695 residue precursor protein called βAPP whose biological functions are not well understood.

Immunocytochemistry of brains affected by Alzheimer's disease has revealed that AβP is widely distributed outside of the senile plaques. There are numerous diffuse deposits of AβP, called diffuse or preamyloid plaques, that contain very few or no surrounding dystrophic nerve cells or glia, and that are found in brain regions that appear to be largely unaffected clinically, such as cerebellum, striatum, and thalamus. Several other distinct proteins are intimately and specifically associated with the β-amyloid deposits, including α-antichymotrypsin, complement factors C1q, C3c and C3d, serum amyloid P protein, and heparan sulfate proteoglycans.

Progressive region-specific loss and degeneration of selected cells in the association and memory areas of the cerebral cortex is seen in Alzheimer's disease, along with abnormalities in certain subcortical nuclei. Neuronal loss affects especially the large pyramidal cells of the parietal and frontal association areas, the hippocampus and amygdala. Strongly affected hippocampal inputs are those from the entorhinal cortex, cholinergic neurons of the basal forebrain, and noradrenergic neurons of the locus coeruleus. The basal forebrain nucleus of Meynert, from which the major cholinergic projection to the cortex arises, also suffers severe degeneration.

Substantial evidence points to a significant role for basal forebrain cholinergic neurons in the behavioral alterations seen in Alzheimer patients. The loss of cholinergic function is one of the earliest changes in the disease. The extent of the cholinergic deficit correlates with the degree of memory impairment, and enhancement of cholinergic function by acetylcholinesterase inhibitors produces modest but significant amelioration of symptoms. In animals, lesions of the cholinergic neurons innervating the hippocampus and cortex result in pronounced memory and cognitive deficits that are reversed by drugs that enhance cholinergic function. (Hefti, *J. Neurobiol.* 25:1418–1435, 1994).

Projection neurons producing other monoamine transmitters (norepinephrine, serotonin, and dopamine) and cortical neurons producing glutamate, gamma-aminobutyric acid (GABA), somatostatin, neuropeptide Y, corticotropin releasing factor, substance P and other neuromodulators are also affected in Alzheimer's disease.

Attempts to ameliorate Alzheimer patients' amnestic and cognitive symptoms by treatment solely with cholinergic drugs have met with little success and result in numerous-side effects. Tacrine hydrochloride (Cognex®), an acetylcholinesterase inhibitor, inhibits the breakdown of acetylcholine and is the only drug approved by the FDA for administration to Alzheimer patients. However, this drug also provides limited improvement and has a number of adverse side effects including significant liver toxicity.

Treatment with neurotrophins, such as NGF, has also been considered for Alzheimer's disease. Some neurotrophins have been shown to have a positive effect in the fimbria/fornix axotomy model of Alzheimer's disease. In this model, when the neurons in the medial septum are axotomized by transection of the fimbria/fornix, the cholinergic neurons quickly, i.e., within 2 weeks, down regulate their expression of p75, trkA, and CHAT. They then become atrophic and unrecognizable as neurons, a state similar to Alzheimer's disease (Batchelor et al., *J. Comp. Neurol.* 284:187–204, 1989; Gage et al., *Neuroscience* 19:241–255, 1986; Hagg et al., *Brain Res.* 505:29–38, 1989; Hefti, *J. Neurosci.* 6:2155–2162, 1986; Springer et al., *J. Neurosci. Res.* 17:111–118, 1987; Sofroniew et al., *J. Neurosci.* 13:5263–5276, 1993). In this model, it has been shown that the axotomy-induced neuronal atrophy could be prevented and the cholinergic phenotype sustained or even augmented by treating the brains with intracerebroventricular doses of NGF, BDNF, or NT-4/5 (Hagg et al., *Brain Res.* 505:29–38, 1989; Hefti, *J. Neurosci.* 6:2155– 2162, 1986; Knusel et al., *J. Neurosci.* 12:4391–4402, 1992; Koliatsos et al., *J. Comp. Neurol.* 343:247–262, 1994; Koliatsos et al., *Ann. Neurol.* 30:831–840, 1991; Morse et al., *J. Neurosci.* 13:4146–4156, 1993; Venero et al., *Neuroscience* 59:797–815, 1994; Widmer et al., *Neuroreport* 4:363–366, 1993; Williams et al., *Brain Research* 498:243–256, 1989; Williams et al., *Proc. Nat. Acad. Sci. (USA)* 83:9231–9235, 1986; Alderson et al., *Eur. J. Neurosci. in press:* 1995). Based on the efficacy of these neurotrophins in reversing the axotomy-induced cholinergic dystrophy, administration of neurotrophins, particularly NGF, has been considered for therapy of Alzheimer's disease and other neurodegenerative disorders (Hefti, *J. Neurobiol.* 25:1418–1435, 1994; Phelps et al., *Neurobiol. Aging* 10:205–207, 1989; Olson, *Neurochem. Jul.* 25:1–3, 1994). In fact, small scale clinical trials testing for such efficacy are ongoing and beginning to be reported (c.f. Olson et al., *J. Neural Transm.* 4:79–95, 1992; Petty et al., *Ann. Aug.* 36:244–246, 1994).

NGF is the most potent neurotrophic factor for basal forebrain neurons of any reported in the literature, and thus was considered to be the neurotrophic factor of choice for the potential treatment of Alzheimer's disease (Olson, *Neurochem. Jul.* 25:1–3, 1994; Olson et al., *J. Neural Transm.* 4:79–95, 1992). Not only does NGF sustain the cholinergic phenotype in animal models of cholinergic dysfunction, but it boosts cholinergic transmission to supra normal levels (Hagg et al., *Neurosci.* 30:95–103, 1989; Hagg et al., *Brain Res.* 505:29–38, 1989; Rylett et al., *J. Neurosci.* 13:3956–3963, 1993; Williams et al., *Brain Research* 498:243–256, 1989; Lapchak, *Exp. Neurol.* 124:16–20, 1993). NGF can also induce structural changes even in normal cholinergic neurons, including hypertrophy of the cell body and increased perineuronal processes (Hagg et al., *Brain Res.* 505:29–38, 1989), and possibly abnormal axonal connections. However, the alteration of cholinergic neuronal structure, abnormal sprouting, and abnormal neurotransmission may be undesirable side effects of NGF therapy (Butcher and Woolf, *Neurobiol. Aging* 10:557–570, 1989). Peripheral NGF is a major contributor to inflammatory pain (Woolf et al., *Neuroscience Sep.* 62:327–331, 1994), and peripheral administration of NGF in rodents induces a hyperalgesia (Della Seta et al., *Pharmacol.* 49:701–705, 1994; Lewin and Mendell, *Trends. Neurosci. Sep.* 16:353–359, 1993).

Untenable side effects have been evident in the initial human clinical trials of NGF, via systemic administration for peripheral neuropathy, and via central administration for Alzheimer's disease. Peripheral administration of NGF in humans at low doses causes severe muscle pain (Petty et al., *Ann. Aug.* 36:244–246, 1994). Alzheimer's patients treated with intracerebroventricular infusions of NGF at the relatively low dose of 66 μg/day (Olson et al., *J. Neural Transm.* 4:79–95, 1992) (a dose comparable, based on brain weight, to a rat dose of 0.08 μg/day (Williams, *Exp. Neurol.* 113:31–37, 1991) experience peripheral rostral muscle pain similar to that reported after peripheral NGF administration (Petty et al., *Ann. Aug.* 36:244–246, 1994), and significant weight loss. Such side effects may disallow the potentially efficacious use of NGF for such therapy.

BDNF is also known to have activity on axotomized basal forebrain cholinergic neurons (for reviews, see Hefti and Lapchak, *Adv. Pharmacol.* 24:239–273, 1993; Lapchak et al., *Exp. Neurol.* 124:16–20, 1993). However, BDNF is much less potent than NGF and does not improve behavior in cognitively impaired aged rats as does NGF (Fischer et al., *Proc. Natl. Acad. Sci. USA* 91:8607–8611, 1994).

Of general interest to the present invention is a report in Schmidt-Kastner et al., *Mol. Brain Res.*, 26:325–330, 1994 that GDNF mRNA became detectable and was upregulated after pilocarpine-induced seizures. Of further interest to the present invention is WO93/06116 (Lin et al., Syntex-Synergen Neuroscience Joint Venture), published Apr. 1, 1993, which reports that GDNF is useful for the treatment of nerve damage and recites, inter alia, Alzheimer's disease as a cause of nerve damage. Also of interest are the reports in Schaar et al., *Exp. Neurol.*, 124:368–371, 1993 and Schaar et al., *Exp. Neurol.*, 130:387–393, 1994 that basal forebrain astrocytes expressed moderate levels of GDNF mRNA under culture conditions, but that GDNF did not alter basal forebrain ChAT activity (the latter finding suggesting that basal forebrain cholinergic neurons are not targets for GDNF).

Thus, there continues to exist a need for methods and therapeutic compositions useful for the treatment of Alzheimer's disease that will improve the progressive memory and cognitive deficits seen in the disease. Such methods and therapeutic compositions ideally will improve the memory and cognitive abilities of patients without resulting in severe adverse side effects.

SUMMARY OF THE INVENTION

The present invention provides a method for treating injury or degeneration of basal forebrain cholinergic neurons by administering a therapeutically effective mount of glial cell line-derived neurotrophic factor (GDNF) protein product. According to one aspect of the invention, methods are provided for treating Alzheimer's disease by administering a therapeutically effective amount of GDNF protein product. It is contemplated that such GDNF protein products would include a GDNF having the amino acid sequence set forth in SEQ ID NO:1, variants, and derivatives thereof. The invention is based on the novel discovery that administration of GDNF protein product promotes the survival and regeneration of damaged basal forebrain cholinergic neurons, which are prominently involved in Alzheimer's disease.

According to the invention, the GDNF protein product is administered at a dose between about 10 µg/kg/day and 100 mg/kg/day, and preferably at a dose between about 1 mg/kg/day and 25 mg/kg/day, and most preferably at a dose between about 5 and 20 mg/kg/day. It is further contemplated that the GDNF protein product be administered with an effective amount of a second therapeutic agent for Alzheimer's disease. Such second therapeutic agents may include cholinergic agonists, cholinesterase inhibitors, and other neurotrophic factors.

The invention also provides for the use of GDNF protein product in the manufacture of a medicament for the treatment of injury or degeneration of basal forebrain cholinergic neurons, including the treatment of Alzheimer's disease.

Numerous additional aspects and advantages of the invention will become apparent to those skilled in the art upon consideration of the following detailed description of the invention which describes presently preferred embodiments thereof.

DETAILED DESCRIPTION OF THE INVENTION

Figure 1:
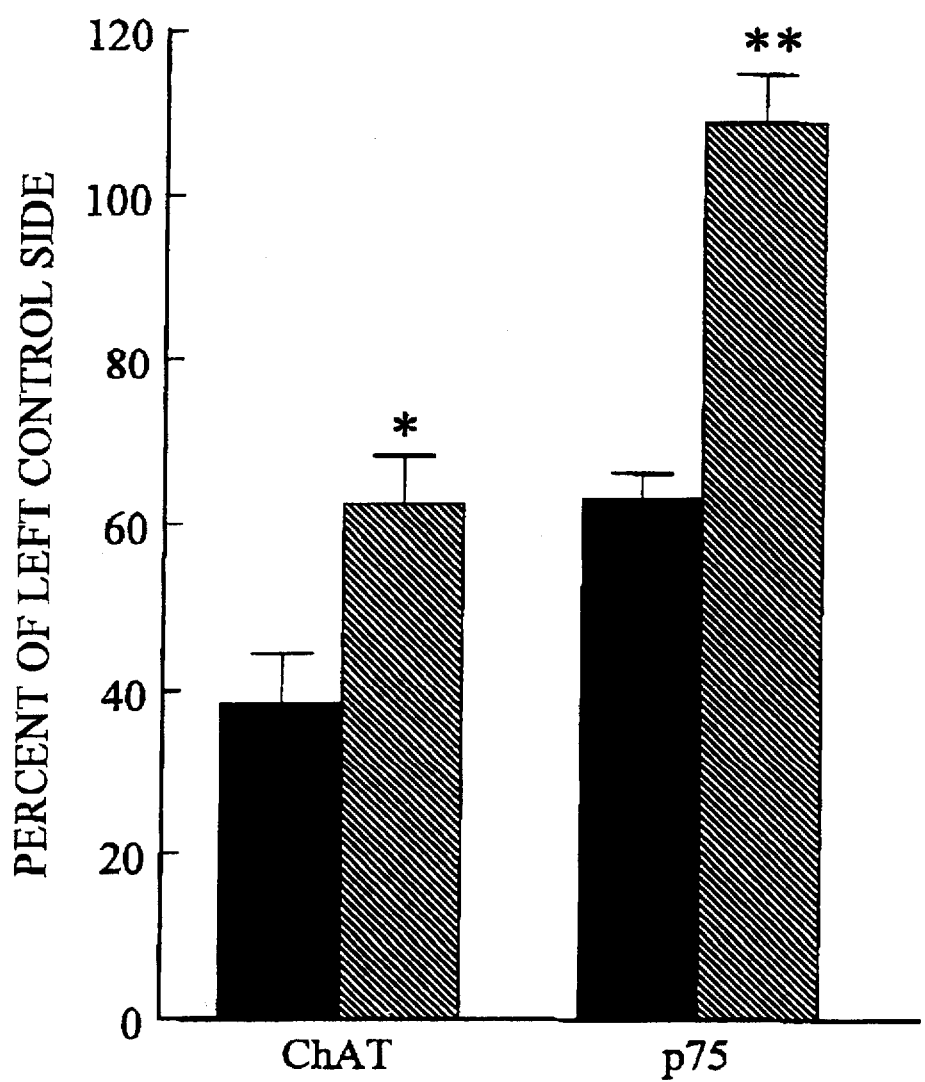
FIG. 1 displays the effect of [Met$^{-1}$]GDNF or vehicle treatment on the number of ChAT- and p75-positive neurons after fimbria/fornix axotomy.

The present invention provides a method for treating injury or degeneration of basal forebrain cholinergic neurons by administering a therapeutically effective amount of glial cell line-derived neurotrophic factor (GDNF) protein product. According to one aspect of the invention, methods are provided for treating Alzheimer's disease by administering a therapeutically effective amount of GDNF protein product. The invention may be practiced using any biologically active GDNF protein product, including a GDNF having the amino acid sequence set forth in SEQ ID NO:1, variants, and derivatives thereof.

The invention is based on the discovery that administration of GDNF protein product has a positive effect on damaged basal forebrain cholinergic neurons, a neuronal population that had not been previously identified as being responsive to GDNF. It is shown herein that GDNF protein product acts by sustaining the expression of receptors involved in neuronal activity, enabling a regenerative response of axonal growth, and enhancing the activity of key enzymes involved in neuronal cholinergic activity. Degeneration of these basal forebrain neurons is a prominent feature of Alzheimer's disease, and factors that sustain these neurons and/or promote their regeneration are expected to be effective for treating the disease, including improving the accompanying cognitive and memory deficits.

According to the invention, the GDNF protein product is administered at a dose between about 10 µg/kg/day and 100 mg/kg/day, and preferably at a dose between about 1 mg/kg/day and 25 mg/kg/day, and most preferably at a dose between about 5 and 20 mg/kg/day. It is further contemplated that the GDNF protein product be administered with an effective amount of a second therapeutic agent for Alzheimer's disease. Such second therapeutic agents may include: cholinergic agonists, particularly those specific to the CNS and not to peripheral muscles, cholinesterase inhibitors such as tacrine hydrochloride, neurotrophins such as NGF, BDNF, NT-3, NT-4/5, basic fibroblast growth factor (bFGF), or ciliary neurotrophic factor (CNTF), inhibitors of senile amyloid plaque formation, inhibitors of PHF formation, inducers of endogenous neurotrophic factor synthesis or production, and transplanted cells that secrete neurotrophic factors (either intrinsically or through recombinant modification). It is likely that maximally effective growth factor therapy of Alzheimer's disease will require protection of all vulnerable neuronal populations, not just cholinergic ones, and may require a combination of growth factors. There is initial evidence that ascending noradrenergic neurons respond to NT-3 and NT-4/5. It has been reported that bFGF protects neurons of the entorhinal cortex from degeneration induced by axotomy in rats, a lesion modeling entorhinal conical degeneration in Alzheimer's disease. CNTF protects adult thalamo-cortical neurons from degeneration after axotomy.

The invention also provides for the use of GDNF protein product in preparation of a medicament for the treatment of injury or degeneration of basal forebrain cholinergic neurons, including the treatment of Alzheimer's disease.

As used herein, the term "GDNF protein product" includes purified natural, synthetic or recombinant GDNF, biologically active GDNF variants (including insertion, substitution and deletion variants), and chemically modified derivatives thereof. Also included are GDNFs that are substantially homologous to the human GDNF having the amino acid sequence set forth in SEQ ID NO:1. GDNF protein products may exist as homodimers or heterodimers in their biologically active form.

The term "biologically active" as used herein means that the GDNF protein product demonstrates similar neurotrophic properties, but not necessarily all of the same properties, and not necessarily to the same degree, as the GDNF having the amino acid sequence set forth in SEQ ID NO:1. The selection of the particular neurotrophic properties of interest depends upon the use for which the GDNF protein product is being administered.

The term "substantially homologous" as used herein means having a degree of homology to the GDNF having the amino acid sequence set forth in SEQ ID NO:1 that is preferably in excess of 70%, most preferably in excess of 80%, and even more preferably in excess of 90% or 95%. For example, the degree of homology between the rat and human protein is about 93%, and all mammalian GDNF will have a similarly high degree of homology. The percentage of homology as described herein is calculated as the percentage of amino acid residues found in the smaller of the two sequences which align with identical amino acid residues in the sequence being compared, when four gaps in a length of 100 amino acids may be introduced to assist in that alignment, as set forth by Dayhoff, in *Atlas of Protein Sequence and Structure* v. 5, p. 124, National Biochemical Research Foundation, Washington, D.C. (1972), the disclosure of which is hereby incorporated by reference. Also included as substantially homologous is any GDNF protein product which may be isolated by virtue of cross-reactivity with antibodies to the GDNF of SEQ ID NO:1 or whose genes may be isolated through hybridization with the gene or with segments of the gene encoding the GDNF of SEQ ID NO:1.

The GDNF protein products according to this invention may be isolated or generated by any means known to those skilled in the art. Exemplary methods for producing GDNF protein products useful in the present invention are described in U.S. patent application Ser. No. 08/182,183 filed May 23, 1994 and its parent applications; PCT Application No. PCT/US92/07888 filed Sep. 17, 1992, published as WO 93/06116 (Lin et al., Syntex-Synergen Neuroscience Joint Venture); European Patent Application No. 92921022.7, published as EP 610 254; and co-owned, co-pending U.S. application Ser. No. 08/535,681 filed concurrently herewith ("Truncated Glial Cell-Line Derived Neurotrophic Factor"), the disclosures of all of which are hereby incorporated by reference.

Naturally-occurring GDNF protein products may be isolated from mammalian neuronal cell preparations, or from a mammalian cell line secreting or expressing GDNF. For example, WO93/06116 describes the isolation of GDNF from serum-free growth conditioned medium of B49 glioblastoma cells. GDNF protein products may also be chemically synthesized by any means known to those skilled in the art. GDNF protein products are preferably produced via recombinant techniques because they are capable of achieving comparatively higher amounts of protein at greater purity. Recombinant GDNF protein product forms include glycosylated and non-glycosylated forms of the protein, and protein expressed in bacterial, mammalian or insect cell systems.

In general, recombinant techniques involve isolating the genes responsible for coding GDNF, cloning the gene in suitable vectors and cell types, modifying the gene if necessary to encode a desired variant, and expressing the gene in order to produce the GDNF protein product. Alternatively, a nucleotide sequence encoding the desired GDNF protein product may be chemically synthesized. It is contemplated that GDNF protein product may be expressed using nucleotide sequences which differ in codon usage due to the degeneracies of the genetic code or allelic variations. WO93/06116 describes the isolation and sequencing of a cDNA clone of the rat GDNF gene, and the isolation, sequencing and expression of a genomic DNA clone of the human GDNF gene. WO93/06116 also describes vectors, host cells, and culture growth conditions for the expression of GDNF protein product. Additional vectors suitable for the expression of GDNF protein product in *E. coli* are disclosed in published European Patent Application No. EP 0 423 980 ("Stem Cell Factor") published Apr. 24, 1991, the disclosure of which is hereby incorporated by reference. The DNA sequence of the gene coding for mature human GDNF and the amino acid sequence of the GDNF is shown in FIG. 19 (SEQ ID NO:5) of WO93/06116. FIG. 19 does not show the entire coding sequence for the pre-pro portion of GDNF, but the first 50 amino acids of human pre-pro GDNF are shown in FIG. 22 (SEQ ID NO:8) of WO93/06116.

Naturally-occurring GDNF is a disulfide-bonded dimer in its biologically active form. The material isolated after expression in a bacterial system is essentially biologically inactive, and exists as a monomer. Refolding is necessary to produce the biologically active disulfide-bonded dimer. Processes for the refolding and naturation of the GDNF expressed in bacterial systems are described in WO93/06116. Standard in vitro assays for the determination of GDNF activity are described in WO93/06116 and co-owned, co-pending U.S. application Ser. No. 08/535,681.

A. GDNF variants

The term "GDNF variants" as used herein includes polypeptides in which amino acids have been deleted from ("deletion variants"), inserted into ("addition variants"), or substituted for ("substitution variants"), residues within the amino acid sequence of naturally-occurring GDNF. Such variants are prepared by introducing appropriate nucleotide changes into the DNA encoding the polypeptide or by in vitro chemical synthesis of the desired polypeptide. It will be appreciated by those skilled in the art that many combinations of deletions, insertions, and substitutions can be made provided that the final molecule possesses GDNF biological activity.

Mutagenesis techniques for the replacement, insertion or deletion of one or more selected amino acid residues are well known to one skilled in the art (e.g., U.S. Pat. No. 4,518,584, the disclosure of which is hereby incorporated by reference.) There are two principal variables in the construction of variants: the location of the mutation site and the nature of the mutation. In designing GDNF variants, the selection of the mutation site and nature of the mutation will depend on the GDNF characteristic(s) to be modified. The sites for mutation can be modified individually or in series, e.g., by (1) substituting first with conservative amino acid choices and then with more radical selections depending upon the results achieved (2) deleting the target amino acid residue, or (3) inserting amino acid residues adjacent to the located site. Conservative changes in from 1 to 20 amino acids are preferred. Once the amino acid sequence of the desired GDNF protein product is determined, the nucleic acid sequence to be used in the expression of the protein is readily determined. N-terminal and C-terminal deletion variants may also be generated by proteolytic enzymes.

For GDNF deletion variants, deletions generally range from about 1 to 30 residues, more usually from about 1 to 10 residues, and typically from about 1 to 5 contiguous residues. N-terminal, C-terminal and internal intrasequence deletions are contemplated. Deletions may be introduced into regions of low homology with other TGF-β family members to modify the activity of GDNF. Deletions in areas of substantial homology with other TGF-b family sequences will be more likely to modify the GDNF biological activity more significantly. The number of consecutive deletions will be selected so as to preserve the tertiary structure of the GDNF protein product in the affected domain, e.g., cysteine crosslinking. Non-limiting examples of deletion variants include truncated GDNF protein products lacking from one to forty N-terminal amino acids of GDNF, or variants lacking the C-terminal residue of GDNF, or combinations thereof, as described in co-owned co-pending U.S. application Ser. No. 08/535,681.

For GDNF addition variants, amino acid sequence additions typically include N- and/or C-terminal fusions ranging in length from one residue to polypeptides containing a hundred or more residues, as well as internal intrasequence additions of single or multiple amino acid residues. Internal additions may range generally from about 1 to 10 residues, more typically from about 1 to 5 residues, and usually from about 1 to 3 amino acid residues. Examples of N-terminal addition variants include GDNF with an N-terminal methionyl residue (an artifact of the direct expression of GDNF in bacterial recombinant cell culture), which is designated [Met$^{-1}$]GDNF, and fusion of a heterologous N-terminal signal sequence to the N-terminus of GDNF to facilitate the secretion of mature GDNF from recombinant host cells. Such signal sequences generally will be obtained from, and thus be homologous to, the intended host cell species. Additions may also include amino acid sequences derived from the sequence of other neurotrophic factors. A preferred GDNF protein product for use according to the present invention is the recombinant human [Met$^{-1}$]GDNF.

GDNF substitution variants have at least one amino acid residue of the GDNF amino acid sequence removed and a different residue inserted in its place. Such substitution variants include allelic variants, which are characterized by naturally-occurring nucleotide sequence changes in the species population that may or may not result in an amino acid change. Examples of substitution variants (see, e.g., SEQ ID NO:50) are disclosed in co-owned, co-pending U.S. application Ser. No. 08/535,681.

Specific mutations of the GDNF amino acid sequence may involve modifications to a glycosylation site (e.g., serine, threonine, or asparagine). The absence of glycosylation or only partial glycosylation results from amino acid substitution or deletion at any asparagine-linked glycosylation recognition site or at any site of the molecule that is modified by addition of an O-linked carbohydrate. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. A variety of amino acid substitutions or deletions at one or both of the first or third amino acid positions of a glycosylation recognition site (and/or amino acid deletion at the second position) result in non-glycosylation at the modified tripeptide sequence. Thus, the expression of appropriate altered nucleotide sequences produces variants which are not glycosylated at that site. Alternatively, the GDNF amino acid sequence may be modified to add glycosylation sites.

One method for identifying GDNF amino acid residues or regions for mutagenesis is called "alanine scanning mutagenesis" as described by Cunningham and Wells (Science, 244:1081–1085, 1989). In this method, an amino acid residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing additional or alternate residues at the sites of substitution. Thus, the target site for introducing an amino acid sequence variation is determined, alanine scanning or random mutagenesis is conducted on the corresponding target codon or region of the DNA sequence, and the expressed GDNF variants are screened for the optimal combination of desired activity and degree of activity.

The sites of greatest interest for substitutional mutagenesis include sites where the amino acids found in GDNF proteins from various species are substantially different in terms of side-chain bulk, charge, and/or hydrophobicity. Other sites of interest are those in which particular residues of GDNF-like proteins, obtained from various species, are identical. Such positions are generally important for the biological activity of a protein. Initially, these sites are substituted in a relatively conservative manner. Such conservative substitutions are shown in Table 1 under the heading of preferred substitutions. If such substitutions result in a change in biological activity, then more substantial changes (exemplary substitutions) are introduced, and/or other additions or deletions may be made, and the resulting products screened for activity.

TABLE 1

Amino Acid Substitutions

| Original Residue | Preferred Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |

TABLE 1-continued

Amino Acid Substitutions

| Original Residue | Preferred Substitutions | Exemplary Substitutions |
|---|---|---|
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Conservative modifications to the amino acid sequence (and the corresponding modifications to the encoding nucleic acid sequences) are expected to produce GDNF protein products having functional and chemical characteristics similar to those of natural GDNF. In contrast, substantial modifications in the functional and/or chemical characteristics of GDNF protein products may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for another. Such substituted residues may be introduced into regions of the GDNF protein that are homologous with other TGF-β proteins, or into the non-homologous regions of the molecule.

B. GDNF Derivatives

Chemically modified derivatives of GDNF or GDNF variants may be prepared by one of skill in the art given the disclosures herein. The chemical moieties most suitable for derivatization include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (i.e., by osmotic pump, or, more preferably, by injection or infusion, or, further formulated for oral, pulmonary or other delivery routes), and determining its effectiveness.

Suitable water soluble polymers include, but are not limited to, polyethylene glycol, copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. For polyethylene glycol, the preferred molecular weight is between about 2 kDa and about 100 kDa for ease in handling and manufacturing (the term "about" indicating that in preparations of polyethylene glycol, some molecules will weigh more, some less, than the stated molecular weight). Other sizes may be used, depending on the desired therapeutic profile (e.g., the duration of sustained release desired, the effects, if any on biological activity, the ease in handling, the degree or lack of antigenicity and other known effects of polyethylene glycol on a therapeutic protein or variant).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. See for example, EP 0 401 384, the disclosure of which is hereby incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydrl groups may also be used as a reactive group for attaching the polyethylene glycol molecule(s). For therapeutic purposes, attachment at an amino group, such as attachment at the N-terminus or lysine group is preferred. Attachment at residues important for receptor binding should be avoided if receptor binding is desired.

One may specifically desire an N-terminal chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the pKa differences between the e-amino group of the lysine residues and that of the a-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

The present invention contemplates use of derivatives which are prokaryote-expressed GDNF, or variants thereof, linked to at least one polyethylene glycol molecule, as well as use of GDNF, or variants thereof, attached to one or more polyethylene glycol molecules via an acyl or alkyl linkage.

Pegylation may be carried out by any of the pegylation reactions known in the art. See, for example: *Focus on Growth Factors*, 3 (2):4–10 (1992); EP 0 154 316, the disclosure of which is hereby incorporated by reference; EP 0 401 384; and the other publications cited herein that relate to pegylation. The pegylation may be carried out via an acylation reaction or an alkylation reaction with a reactive polyethylene glycol molecule (or an analogous reactive water-soluble polymer).

Pegylation by acylation generally involves reacting an active ester derivative of polyethylene glycol (PEG) with the GDNF protein or variant. Any known or subsequently discovered reactive PEG molecule may be used to carry out the pegylation of GDNF protein or variant. A preferred activated PEG ester is PEG esterified to N-hydroxysuccinimide ("NITS"). As used herein, "acylation" is contemplated to include without limitation the following types of linkages between the therapeutic protein and a water soluble polymer such as PEG: amide, carbamate, urethane, and the like. See *Bioconjugate Chem.*, 5:133–140 (1994). Reaction conditions may be selected from any of those known in the pegylation art or those subsequently developed, but should avoid conditions such as temperature, solvent, and pH that would inactivate the GDNF or variant to be modified.

Pegylation by acylation will generally result in a poly-pegylated GDNF protein or variant. Preferably, the connecting linkage will be an amide. Also preferably, the resulting product will be substantially only (e.g., >95%) mono, di- or tri- pegylated. However, some species with higher degrees of pegylation may be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with the GDNF protein or variant in the presence of a reducing agent. Pegylation by alkylation can also result in poly-pegylated GDNF protein or variant. In addition, one can manipulate the reaction conditions to favor pegylation substantially only at the a-amino group of the N-terminus of the GDNF protein or variant (i.e., a mono-pegylated protein). In either case of monopegylation or polypegylation, the PEG groups are preferably attached to the protein via a —CH2—NH— group. With particular reference to the —CH2— group, this type of linkage is referred to herein as an "alkyl" linkage.

Derivatization via reductive alkylation to produce a monopegylated product exploits differential reactivity of different types of primary amino groups (lysine versus the N-terminal) available for derivatization. The reaction is performed at a pH which allows one to take advantage of the pKa differences between the e-amino groups of the lysine residues and that of the a-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs. In one important aspect, the present invention contemplates use of a substantially homogeneous preparation of monopolymer/GDNF protein (or variant) conjugate molecules (meaning GDNF protein or variant to which a polymer molecule has been attached substantially only (i.e., >95%) in a single location). More specifically, if polyethylene glycol is used, the present invention also encompasses use of pegylated GDNF protein or variant lacking possibly antigenic linking groups, and having the polyethylene glycol molecule directly coupled to the GDNF protein or variant.

Thus, presently preferred GDNF protein products according to the present invention are pegylated GDNF protein or variants, wherein the PEG group(s) is (are) attached via acyl or alkyl groups. As discussed above, such products may be mono-pegylated or poly-pegylated (e.g., containing 2–6, and preferably 2–5, PEG groups). The PEG groups are generally attached to the protein at the a- or e-amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches may be selected from among water soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1–C10 alkoxy or aryloxy derivatives thereof (see, U.S. Pat. No. 5,252,714). The polymer may be branched or unbranched. For the acylation reactions, the polymer(s) selected should have a single reactive ester group. For the present reductive alkylation, the polymer(s) selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

A particularly preferred water-soluble polymer for use herein is polyethylene glycol. As used herein, polyethylene glycol is meant to encompass any of the forms of PEG that have been used to derivatize other proteins, such as mono-(C 1–C 10) alkoxy- or aryloxy-polyethylene glycol.

In general, chemical derivatization may be performed under any suitable condition used to react a biologically active substance with an activated polymer molecule. Methods for preparing pegylated GDNF protein or variant will generally comprise the steps of (a) reacting a GDNF protein or variant with polyethylene glycol (such as a reactive ester or aldehyde derivative of PEG) under conditions whereby the protein becomes attached to one or more PEG groups, and (b) obtaining the reaction product(s). In general, the optimal reaction conditions for the acylation reactions will be determined case-by-case based on known parameters and the desired result. For example, the larger the ratio of PEG:protein, the greater the percentage of poly-pegylated product.

Reductive alkylation to produce a substantially homogeneous population of mono-polymer/GDNF protein (or variant) conjugate molecule will generally comprise the steps of: (a) reacting a GDNF protein or variant with a reactive PEG molecule under reductive alkylation conditions, at a pH suitable to permit selective modification of the a-amino group at the amino terminus of said GDNF protein or variant; and (b) obtaining the reaction product(s).

For a substantially homogeneous population of mono-polymer/GDNF protein (or variant) conjugate molecules, the reductive alkylation reaction conditions are those which permit the selective attachment of the water soluble polymer moiety to the N-terminus of GDNF protein or variant. Such reaction conditions generally provide for pKa differences between the lysine amino groups and the a-amino group at the N-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal a-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6.

Another important consideration is the molecular weight of the polymer. In general, the higher the molecular weight of the polymer, the fewer polymer molecules may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa. The preferred average molecular weight is about 5 kDa to about 50 kDa, particularly preferably about 12 kDa to about 25 kDa. The ratio of water-soluble polymer to GDNF protein or variant will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any GDNF protein or variant having an a-amino group at the amino terminus, and provide for a substantially homogenous preparation of monopolymer/GDNF protein (or variant) conjugate. The term "monopolymer/GDNF protein (or variant) conjugate" is used here to mean a composition comprised of a single polymer molecule attached to a molecule of GDNF protein or GDNF variant protein. The monopolymer/GDNF protein (or variant) conjugate preferably will have a polymer molecule located at the N-terminus, but not on lysine amino side groups. The preparation will preferably be greater than 90% monopolymer/GDNF protein (or variant) conjugate, and more preferably greater than 95% monopolymer/GDNF protein (or variant) conjugate, with the remainder of observable molecules being unreacted (i.e., protein lacking the polymer moiety).

For the present reductive alkylation, the reducing agent should be stable in aqueous solution and preferably be able to reduce only the Schiff base formed in the initial process of reductive alkylation. Preferred reducing agents may be selected from sodium borohydride, sodium cyanoborohydride, dimethylamine borane, trimethylamine borane and pyridine borane. A particularly preferred reducing agent is sodium cyanoborohydride. Other reaction parameters, such as solvent, reaction times, temperatures, etc., and means of purification of products, can be determined case-by-case based on the published information relating to derivatization of proteins with water soluble polymers (see the publications cited herein).

C. GDNF Protein Product Pharmaceutical Compositions

GDNF protein product pharmaceutical compositions typically include a therapeutically effective amount of a GDNF protein product in admixture with one or more pharmaceutically and physiologically acceptable formulation materials. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial CSF, possibly supplemented with other materials common in compositions for parenteral administration. Neutral buffered saline or saline mixed with serum albumin are further exemplary vehicles.

The primary solvent in a vehicle may be either aqueous or non-aqueous in nature. In addition, the vehicle may contain other pharmaceutically-acceptable excipients for modifying or maintaining the pH, osmolarity, viscosity, clarity, color, sterility, stability, rate of dissolution, or odor of the formulation. Similarly, the vehicle may contain still other pharmaceutically-acceptable excipients for modifying or maintaining the rate of release of GDNF protein product, or for promoting the absorption or penetration of GDNF protein product across the blood-brain barrier. Such excipients are those substances usually and customarily employed to formulate dosages for parenteral administration in either unit dose or multi-dose form or for direct continuous or periodic infusion from an implanted pump.

Once the therapeutic composition has been formulated, it may be stored in sterile vials as a solution, suspension, gel, emulsion, solid, or dehydrated or lyophilized powder. Such formulations may be stored either in a ready to use form or in a form, e.g. lyophilized, requiring reconstitution prior to administration.

The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. The material may be incorporated into particulate preparations of polymeric compounds such as polylactic acid, polyglycolic acid, etc. or into liposomes. Hylauronic acid may also be used, and this may have the effect of promoting sustained duration in the circulation. Such compositions may influence the physical state, stability, rate of in vivo release, and rate of in vivo clearance of the present proteins and derivatives.

Other effective administration forms, such as parenteral slow-release formulations, inhalant mists, orally active formulations, or suppositories, are also envisioned. The preferred GDNF protein product pharmaceutical composition is formulated for parenteral administration, e.g. by intracerebroventricular infusion or injection. Such parenterally administered therapeutic compositions are typically in the form of a pyrogen-free, parenterally acceptable aqueous solution comprising the GDNF protein product in a pharmaceutically acceptable vehicle. One preferred vehicle is physiological saline.

It is also contemplated that certain formulations containing GDNF protein product are to be administered orally. GDNF protein product which is administered in this fashion may be encapsulated and may be formulated with or without those carriers customarily used in the compounding of solid dosage forms. The capsule may designed to release the active portion of the formulation at the point in the gastrointestinal tract when bioavailability is maximized and pre-systemic degradation is minimized. Additional excipients may be included to facilitate absorption of GDNF protein product. Diluents, flavorings, low melting point waxes, vegetable oils, lubricants, suspending agents, tablet disintegrating agents, and binders may also be employed.

D. Administration of GDNF Protein Product

The GDNF protein product may be administered parenterally via a subcutaneous, intramuscular, intravenous, transpulmonary, transdermal, intrathecal or intracerebral route. Protein growth factors that do not cross the blood-brain barrier may be given directly intracerebrally or otherwise in association with other elements that will transport them across the barrier. It is preferred that the GDNF protein product is administered intracerebroventricularly or into the brain or spinal cord subarachnoid space. GDNF protein product may also be administered intracerebrally directly into the brain parenchyma. Slow-releasing implants in the brain containing the neurotrophic factor embedded in a biodegradable polymer matrix can also deliver GDNF protein product. GDNF protein product may be administered extracerebrally in a form that has been modified chemically or packaged so that it passes the blood-brain barrier, or it may be administered in connection with one or more agents capable of promoting penetration of GDNF protein product across the barrier. For example, a conjugate of NGF and monoclonal anti-transferrin receptor antibodies has been shown to be transported to the brain via binding to transferrin receptors. To achieve the desired dose of GDNF protein product, repeated daily or less frequent injections may be administered, or GDNF protein may be infused continuously or periodically from a constant- or programmable-flow implanted pump. The frequency of dosing will depend on the pharmacokinetic parameters of the GDNF protein product as formulated, and the route of administration.

Regardless of the manner of administration, the specific dose is typically calculated according to body weight or body surface area. For diseases involving the brain, the specific dose is typically calculated according to the approximate brain weight of the patient, which may be estimated based on body weight or body surface area. Further refinement of the calculations necessary to determine the appropriate dosage for treatment involving each of the above mentioned formulations is routinely made by those of ordinary skill in the art and is within the ambit of tasks routinely performed by them without undue experimentation, especially in light of the dosage information and assays disclosed herein. Appropriate dosages may be ascertained through use of the established assays for determining dosages utilized in conjunction with appropriate dose-response data.

The final dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. As studies are conducted, further information will emerge regarding the appropriate dosage levels for the treatment of various diseases and conditions.

It is envisioned that the continuous administration or sustained delivery of GDNF may be advantageous for a given treatment. While continuous administration may be accomplished via a mechanical means, such as with an infusion pump, it is contemplated that other modes of continuous or near continuous administration may be practiced. For example, chemical derivatization may result in sustained release forms of the protein which have the effect of continuous presence in the blood stream, in predictable amounts, based on a determined dosage regimen. Thus, GDNF protein products include proteins derivatized to effectuate such continuous administration.

GDNF protein product cell therapy, e.g., intracerebral implantation of cells producing GDNF protein product, is also contemplated. This embodiment would involve implanting into patients cells capable of synthesizing and secreting a biologically active form of GDNF protein product. Such GDNF protein product-producing cells may be cells that are natural producers of GDNF protein product (analogous to B49 glioblastoma cells) or may be recombinant cells whose ability to produce GDNF protein product has been augmented by transformation with a gene encoding the desired GDNF protein product in a vector suitable for promoting its expression and secretion. In order to minimize a potential immunological reaction in patients being administered GDNF protein product of a foreign species, it is preferred that the natural cells producing GDNF protein product be of human origin and produce human GDNF protein product. Likewise, it is preferred that the recombinant cells producing GDNF protein product be transformed with an expression vector containing a gene encoding a human GDNF protein product. Implanted cells may be encapsulated to avoid infiltration of brain tissue. Human or non-human animal cells may be implanted in patients in biocompatible, semipermeable polymeric enclosures or membranes that allow release of GDNF protein product, but that prevent destruction of the cells by the patient's immune system or by other detrimental factors from the surrounding tissue. Alternatively, the patient's own cells, transformed to produce GDNF protein product ex vivo, could be implanted directly into the patient without such encapsulation.

GDNF protein product gene therapy in vivo is also envisioned, by introducing the gene coding for GDNF protein product into targeted brain cells via local injection of a nucleic acid construct or other appropriate delivery vectors. (Hefti, *J. Neurobiol.* 25:1418–1435, 1994). For example, a nucleic acid sequence encoding a GDNF protein product may be contained in an adeno-associated virus vector for delivery into the brain or targeted brain cells. Alternative viral vectors include, but are not limited to, retrovirus, adenovirus, herpes simplex virus and papilloma virus vectors. Physical transfer may also be achieved by liposome-mediated transfer, direct injection (naked DNA), receptor-mediated transfer (ligand-DNA complex), electroporation, calcium phosphate precipitation or microparticle bombardment (gene gun).

The methodology for the membrane encapsulation of living cells is familiar to those of ordinary skill in the art, and the preparation of the encapsulated cells and their implantation in patients may be accomplished without undue experimentation. See, e.g., U.S. Pat. Nos. 4,892,538, 5,011, 472, and 5,106,627, each of which is specifically incorporated herein by reference. A system for encapsulating living cells is described in PCT Application WO 91/10425 of Aebischer et al., specifically incorporated herein by reference. See also, PCT Application WO 91/10470 of Aebischer et al., Winn et al., *Exper. Neurol.*, 113:322–329, 1991, Aebischer et al., *Exper. Neurol.*, 111:269–275, 1991; Tresco et al., *ASAIO*, 38:17–23, 1992, each of which is specifically incorporated herein by reference.

It should be noted that the GDNF protein product formulations described herein may be used for veterinary as well as human applications and that the term "patient" should not be construed in a limiting manner. In the case of veterinary applications, the dosage ranges should be the same as specified above.

Other aspects and advantages of the present invention will be understood upon consideration of the following illustrative examples. Example 1 addresses the effect of GDNF protein product or vehicle administration in the rat basal forebrain fimbria/fornix axotomy model. Example 2 compares the effect of NGF, GDNF protein product and BDNF in the rat basal forebrain fimbria/fornix axotomy model. Example 3 addresses the effect of GDNF protein product in a rat age-related dementia model.

EXAMPLE 1

In this first experiment, treatment with GDNF protein product or vehicle was evaluated for its effect on the loss of p75-positive and ChAT-positive neurons in the rat fimbria/fornix axotomy model. The GDNF protein product tested was recombinant human [Met$^{-1}$]GDNF and was produced by expression in *E. coli* as generally described in Examples 6B and 6C of WO93/06116. The protein was refolded and purified to greater than 95% purity as assessed by SDS-PAGE. Bioactivity of the protein was confined in standard in vitro neuronal assays described in Example 4 of co-owned, co-pending U.S. application Ser. No. 08/535,681. The concentration of pure [Met$^{-1}$]GDNF in a stock solution of PBS was determined by molar extinction where an O.D.$_{280}$ of 0.3645 was equivalent to a 1 mg/ml concentration of [Met$^{-1}$]GDNF. Working solutions were prepared by dilution of the concentrate in infusion vehicle, i.e., Dulbecco's PBS containing 0.1% rat serum albumin.

Male Wistar rats (300–350 g, Harlan Sprague-Dawley, Indianapolis, Ind.) were used. Each animal had free access to water and was fed ad libitum on a modified laboratory diet (Purina Laboratory Chow 5001, Richmond, Ind.). The rats were anesthetized with isoflurane gas anesthesia, and positioned in a stereotaxic apparatus according to Paxinos and Watson, *Academic Press, Inc. San Diego*, 1986. The fimbria/fornix of each rat's brain was axotomized using a Scouten knife (Kopf Instruments, Tujunga, Calif.) according to the procedure of Venero et al. *Neuroscience* 59:797–815, 1994.

Immediately following the transection, a 28 gauge stainless steel cannula device with a 4.5 mm length (Plastics One, Roanoke, Va.) was prefilled with either vehicle or [Met$^{-1}$] GDNF, connected to a Model 2002 Alzet osmotic infusion pump (0.5 µl/hr, Alza Corp., Palo Alto, Calif.), and positioned into the right lateral ventricle 0.3 mm posterior and 1.4 mm lateral to bregma. The device was stabilized onto the skull surface with cyanoacrylate glue and dental acrylic with one skull screw. At completion of surgery, the starting body weight of the animal was measured and recorded.

Four rats were treated with [Met$^{-1}$]GDNF at 10 µg/day via continuous intracerebroventricular infusion, a dose comparable to that previously reported for the in vivo efficacy of GDNF on mesencephalic dopaminergic neurons (Hoffer et al., *Neurosci. Lett.* 182:107–111, 1994; Hudson et al., *Brian Res. Bull.* 36:425–432, 1995; Kearns and Gash, *Brain Res.* 672:104–111, 1995; Strumberg et al., *Exp. Neurol.* 124:401–412, 1995). Four control rats were administered vehicle, the 1 mg/ml albumin serving as a non-specific protein. After two weeks of treatment, the animals were prepared for biochemical or morphological end point analysis.

For biochemical analysis of ChAT enzyme activity, unanesthetized rats were decapitated with a Harvard guillotine. The right and left hippocampus and the right and left septal area were dissected from animals treated with 10 µg/day [Met$^{-1}$]GDNF and frozen. Hippocampal and septal tissues were homogenized (20×) in 0.2M Tris-HCl, pH 7.4. Two 5 µl aliquots of this homogenate (2.56 mg/ml) were used for measurement of ChAT activity, using the methods of Schrier and Shuster, *J. Neurochem.* 14: 977–985, 1967. Enzyme specific activity was expressed as the nmol of acetylcholine produced per mg protein per hour. The identity of the individual samples was unknown to the person running the assays.

For morphological analysis, the rats were anesthetized with an intramuscular injection of a mixture (4 ml/kg) of ketamine (25 mg/ml, rompun (1.3 mg/ml) and acepromazine (0.25 mg/ml), weighed, and perfused through the heart with PBS solution followed by 4% paraformaldehyde. Two hours after fixation and equilibration with 30% sucrose, serial 50 µm sliding microtome sections were cut through the basal forebrain and stained immunohistochemically for ChAT and p75. ChAT antibody (MAb 305, Chemicon International, Inc., Temecula, Calif), and p75 antibody (Boehringer Mannheim, Indianapolis, Ind.) were both used at a dilution of 1:1000. Biotinylated secondary antibody and peroxidase-labeled strepavidin (Dako Corp., Carpinteria, Calif.) were used to visualize the localization of both antibodies using 3,3'-diaminobenzidine tetrachloride (Sigma, St. Louis, Mo.) as the substrate.

Because the extent of neuronal atrophy and phenotype down-regulation following axotomy is uniform across the rostral-caudal extent of the septum and diagonal band, only one section from each brain was used for expedient quantitative analysis. The section used corresponded to FIG. 16 or 17 of Paxinos and Watson, *Academic Press, Inc. San Diego*, 1986, a region of maximal neuronal number that is representative of the basal forebrain response to axotomy (Williams et al., *Proc. Nat. Acad. Sci.* (*USA*) 83:9231–9235, 1986; Hagg et al., *Brain Res.* 505:29–38, 1989; Koliatsos et al., *J. Comp. Neurol.* 343:247–262, 1994). Both ChAT-positive and p75-positive cell numbers in the right and left septum and diagonal band were counted manually using a 10× objective (Williams et al., *Proc. Nat. Acad. Sci.* (*USA*) 83:9231–9235, 1986); the investigator was blinded to the identity of the treatment group. The relative optical density (O.D.) of immunohistochemical reaction product in the right and left, medial and lateral septum, and the area of the right and left lateral septum were measured using a computer-assisted image analysis system (MCID, Imaging Research, St. Catherine, Ontario, Canada) (Vahlsing et al., *Brain Research* 552:320–329, 1991). Relative O.D. provides an approximate linear measure of optical density (Smolen, *Neurosciences*, ed. by P.M. Conn, pp. 208–229, Academic Press, Inc. San Diego, Calif., 1990). Micrographs documenting the effects of axotomy and neurotrophic factor treatment were taken with a Kodak DCS 420 digital camera and printed with a Kodak XLS 8600 printer.

All measurements taken from the right axotomized side of histologic sections (except for normal animals) were normalized as the percent of the contralateral unlesioned control side. The changes in animal body weight over a two week period were expressed as the percent of the starting weight. The biochemical measurements were illustrated as the changes in experimental groups as a percent of the values measured in control, untreated tissue. Statistical significance was determined by one way ANOVA using Tukey's HSD test for post hoc analysis (Systat, SPSS Inc., Chicago, Ill.).

The results of this first experiment, presented as the percent ratio of the number of ChAT- or p75-positive neurons counted on the side ipsilateral to the axotomy compared to the number counted on the contralateral unlesioned control side, are displayed in FIG. 1. The data for vehicle-treated animals is displayed in solid bars and that for the [Met$^{-1}$] GDNF-treated animals is displayed in striped bars. (The symbol (*) signifies $p<0.05$, and the symbol (**) signifies $p<0.01$.) In the vehicle-treated animals, there was an apparent loss of 40% of the ChAT-positive and 60% of the p75-positive neurons in the septum and diagonal band ipsilateral to the axotomy. Infusion of [Met$^{-1}$]GDNF limited the loss of ChAT-positive neurons to 60% of normal and prevented the loss of p75-positive neurons (i.e., [Met$^{-1}$] GDNF sustained the expression of p75 immunoreactivity in 100% of the neurons ipsilateral to the transection). In addition, an accumulation of p75-positive immunoreactivity was observed in the lateral septum of [Met$^{-1}$]GDNF-treated rats ipsilateral and proximal to the fimbria/fornix axotomy.

EXAMPLE 2

A larger series of experiments were conducted to evaluate the efficacy and potency of GDNF protein product relative to the neurotrophins NGF and BDNF, using a variety of end points associated with the rat fimbria/fornix axotomy model and a neurotrophic factor dose range of 100 µg/day to 0.1 µg/day. The GDNF protein product tested was recombinant human [Met$^{-1}$]GDNF.

The recombinant human proteins, GDNF protein product, BDNF, and NGF, used in these experiments were produced by expression in *E. coli*. All proteins were refolded and purified to greater than 95% purity as assessed by SDS-PAGE. The bioactivity of the proteins was confirmed in standard in vitro neuronal assays. The activity of [Met$^{-1}$] GDNF was confirmed as described above in Example 1, while the activity of NGF and BDNF was assayed on transformed fibroblast cells expressing the trkA or trkB receptors, respectively. The concentration of pure neurotrophic factor in a stock solution of PBS was determined by molar extinction where an O.D.$_{280}$ of 0.3645 was equivalent to 1 mg/ml [Met$^{-1}$]GDNF, an O.D.$_{280}$ of 1.76 was equivalent to 1 mg/ml BDNF, and an O.D.$_{280}$ of 1.57 was equivalent to 1 mg/ml NGF. Working solutions were prepared by dilution of the concentrate in infusion vehicle, i.e., Dulbecco's PBS containing 0.1% rat serum albumin. No loss of biological activity was detected in sterile aliquots of working solutions of [Met$^{-1}$]GDNF, BDNF, or NGF when stored in vitro at 37° C. for periods up to 1 month. No loss in biological activity was detected in 100 µg/ml [Met$^{-1}$] GDNF solutions after two weeks infusion in vivo.

Doses of [Met$^{-1}$]GDNF and BDNF ranging from 100 µg/day to 0.1 µg/day were evaluated in this model, in order to compare the dose response curves for the two neurotrophic factors. Because the dose response curves for NGF in this model have been reported previously (Emmett et al., *Brain Res.* 673:199–207, 1995; Williams et al., *Brain Research* 498:243–256, 1989), only maximally effective doses of NGF were examined in the present experiments, i.e., doses of 1 µg/day and 10 µg/day. Control animals were administered vehicle, the albumin (1 mg/ml) serving as a non-specific protein.

The experiments were conducted according to the procedures described in Example 1, except that the method of axotomy was modified to enable a more consistent and complete transection of the fimbria/fornix and a greater loss of neuronal markers than observed in the first experiment. Axotomy was performed as follows. A small slit was drilled into the skull beginning 1.0 mm posterior and 1.0 mm lateral to bregma extending 2.0 mm lateral to bregma. Complete axotomy of the fimbria/fornix was achieved using two overlapping Scouten knife cuts. For the first cut, the retracted knife was positioned at 1.0 mm posterior, 2.0 mm lateral to bregma and lowered 6.0 mm ventral of the dura mater. The first cut was executed by the following manual steps: extend knife 2.0 mm towards the midline; raise knife 4.5 mm; retract and re-extend knife; lower knife 4.5 mm; retract and extend knife again; raise knife 4.5 mm; retract and remove knife. For the second overlapping cut, the knife was rotated 180° so that the blade now extended laterally. The knife was positioned 1.0 mm posterior and 1.4 mm lateral to bregma, and lowered 6.0 mm ventral to the surface of the dura. The second cut was executed by the following manual steps: laterally extend knife 2.0 mm; raise knife 4.5 mm; retract and re-extend knife; lower knife 4.5 mm; retract and extend knife again; raise knife 4.5 mm; retract and remove knife. This sequence resulted in a 100% transection of the fimbria/fornix as determined by visual inspection of practice animals, and a greater than 90% loss of ChAT biochemical activity in the hippocampus ipsilateral to the axotomy.

Figure 2:
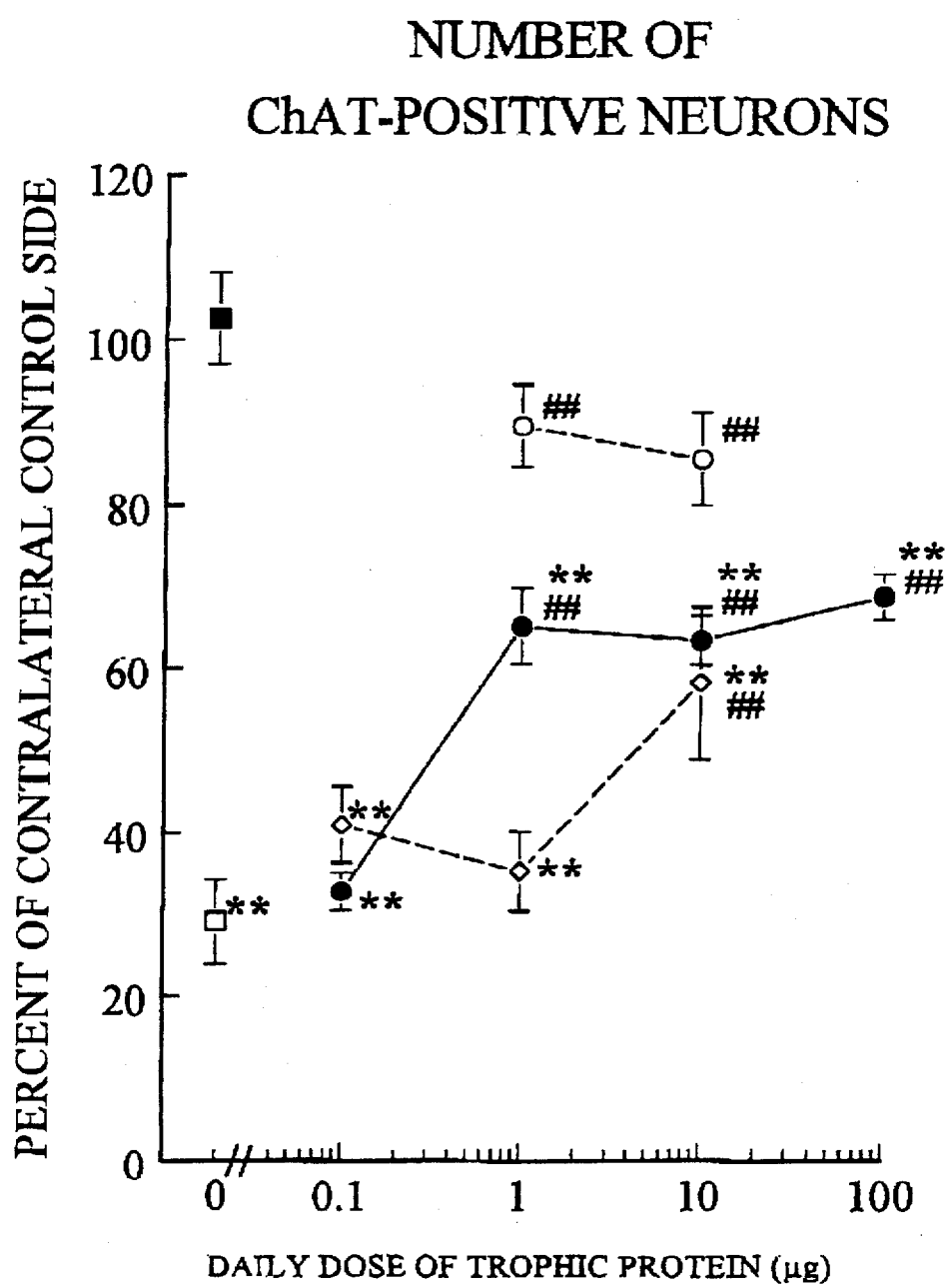
FIG. 2 displays the effect of [Met$^{-1}$]GDNF, BDNF, NGF or vehicle treatment on the number of ChAT-positive neurons after fimbria/fornix axotomy.

FIG. 2 displays the dose response curves for [Met$^{-1}$] GDNF (closed circles), NGF (open circles), and BDNF (open diamonds) on the number of ChAT immunoreactive neurons after axotomy (sample n=10 for all doses except for: normal, n=6; and BDNF at 0.1 µg/day, n=4). The data is expressed as the percent ratio (mean±SEM) of the number of ChAT-positive neurons counted on the right side ipsilateral to the axotomy compared to the number counted on the contralateral control side. (The symbol (**) signifies $p<0.01$ compared to normal animals, and the symbol (##) signifies $p<0.01$ compared to vehicle-treated animals.) In vehicle-treated animals (open squares), only 30% of the normal population of neurons (closed squares) were ChAT-positive two weeks after axotomy. [Met$^{-1}$]GDNF and BDNF treatment at the maximally effective dose sustained ChAT expression in 60% of the neurons, while NGF treatment at the maximally effective dose sustained ChAT expression in 90% of the neurons. For [Met$^{-1}$]GDNF, maximum efficacy was attained at doses greater than 1 µg/day, and efficacy dropped to vehicle control levels at lower doses. For BDNF, maximum efficacy was attained at 10 µg/day, but this effect was lost at the lower doses of 1 and 0.1 µg/day.

On histological examination, in vehicle-treated animals there was an obvious loss of ChAT-positive neurons on the side ipsilateral to the axotomy compared to the contralateral side. Treatment with [Met$^{-1}$]GDNF at 1 µg/day, NGF at 1 µg/day, and BDNF at 10 µg/day significantly reduced the loss of ChAT-positive neurons, sustaining the cholinergic phenotype in the axotomized cells. The apparent expression of ChAT immunoreactivity and size of the [Met$^{-1}$]GDNF-treated, axotomized neurons were similar to that observed in normal untreated animals, in vehicle-treated animals, and on the contralateral control side. The apparent expression of ChAT immunoreactivity and size of the NGF-treated neurons was greater than those in normal and vehicle-treated animals, and the effect was bilateral.

Quantitative densitometry of ChAT immunoreactivity in the medial septum and diagonal band indicated that this was not a useful indicator of axotomy-induced ChAT down-regulation or neurotrophic sustenance, i.e., the background immunoreactivity did not enable the resolution of an apparent decrease in density on the side of axotomy in vehicle-treated animals, nor did it resolve any apparent increase in density due to any neurotrophic factor treatment compared to the contralateral side. In addition, the ChAT-specific antibody revealed no evidence of ChAT immunoreactive sprouts in the lateral septum ipsilateral to the axotomy.

Figure 3:
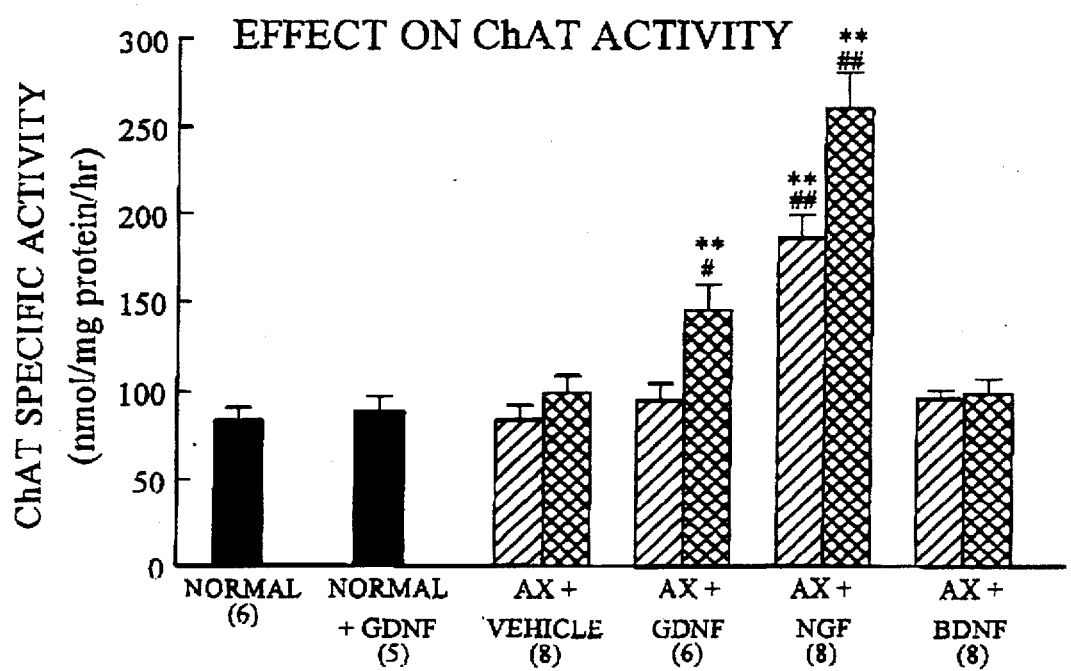
FIG. 3 displays the effect of 10 µg/day of [Met$^{-1}$]GDNF, BDNF, NGF or vehicle on ChAT enzyme activity after fimbria/fornix axotomy.

FIG. 3 displays the effect of the neurotrophic factors on ChAT biochemical specific activity in the septal area of normal animals (solid bar), or in the septum of axotomized animals both on the left side contralateral to the axotomy (single hatched bar) and on the right side ipsilateral to the axotomy (double hatched bars). Sample size is shown in parentheses below each bar. (The symbol (**) signifies $p<0.01$ compared to normal animals, the symbol (##) signifies $p<0.01$ compared to vehicle-treated animals, and the symbol (#) signifies $p<0.05$ compared to vehicle-treated animals.) There was no loss of ChAT enzyme activity in the right septal area ipsilateral to the transection. [Met$^{-1}$]GDNF treatment at 10 μg/day resulted in an axotomy-dependent enhancement of ChAT activity; there was no effect in normal animals or in the contralateral control side, but there was a significantly elevated ChAT activity ipsilateral to the axotomy that was 40% greater than that observed in normal and vehicle-treated animals. NGF treatment resulted in enhanced levels of ChAT activity in both the left control septum and the right septum ipsilateral to the axotomy, to levels 2.2-fold and 3.1-fold greater than normal, respectively. Similar treatment with BDNF at 10 μg/day had no effect on ChAT enzyme activity.

Figure 4:
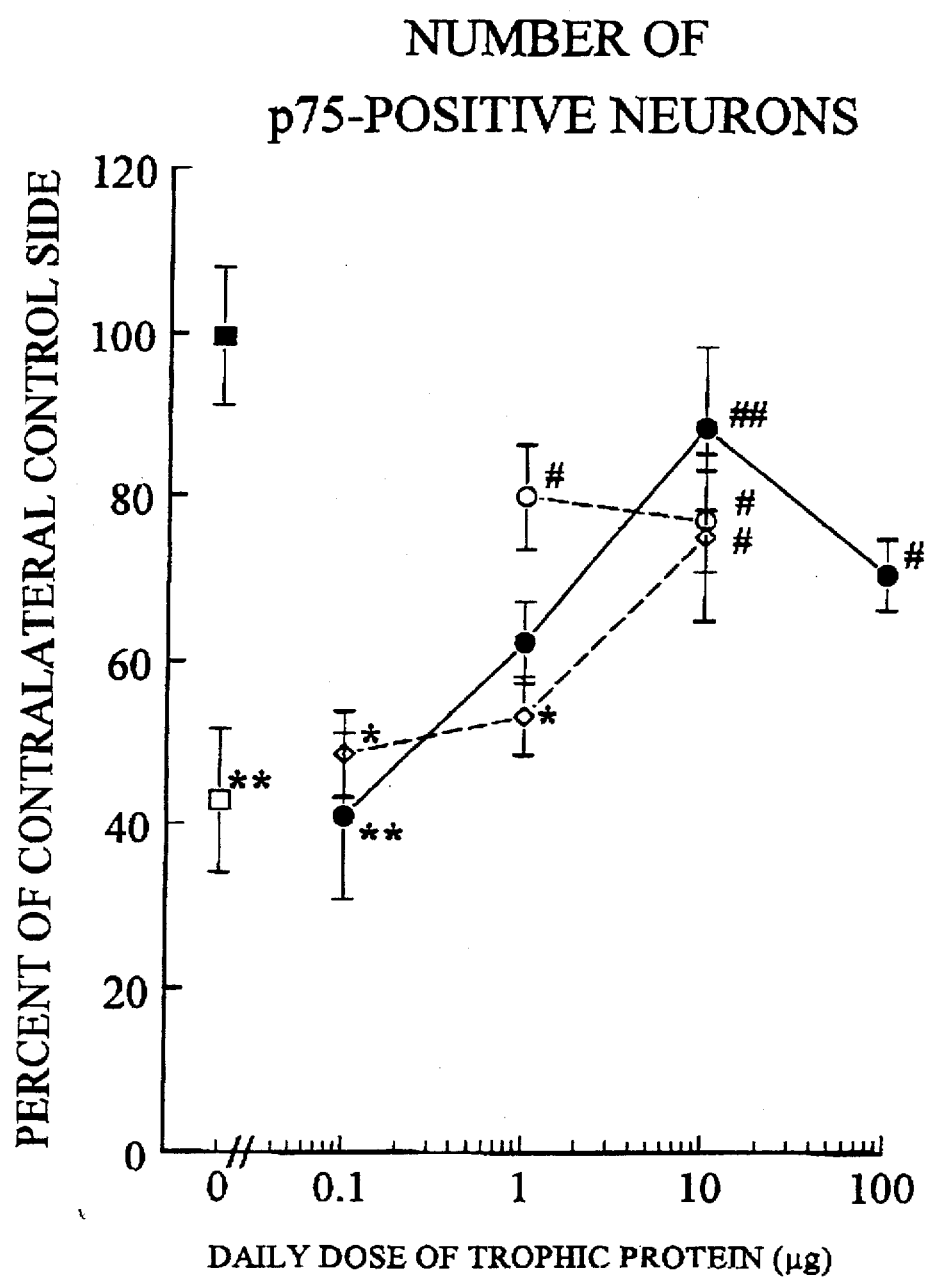
FIG. 4 displays the effect of [Met$^{-1}$]GDNF, BDNF, NGF or vehicle treatment on the number of p75-positive neurons after fimbria/fornix axotomy.

FIG. 4 displays the effect of [Met$^{-1}$]GDNF (closed circles), NGF (open circles), and BDNF (open diamonds) on the number of p75 immunoreactive neurons after axotomy (sample n=10 except for: normal, n=6; and BDNF at 0.1 μg/day, n=4). The data is expressed as the percent ratio (mean±SEM) of the number of p75-positive neurons counted on the right side ipsilateral to the axotomy compared to the number counted on the contralateral control side. (The symbol (**) signifies $p<0.01$ compared to normal animals, and the symbol (##) signifies $p<0.01$ compared to vehicle-treated animals.) In vehicle-treated animals (open squares), only 40% of the normal population (closed squares) were immunoreactive for p75 two weeks after axotomy. The maximally effective [Met$^{-1}$]GDNF treatment, at a dose of 10 μg/day, sustained p75 expression in 90% of the basal forebrain neurons. [Met$^{-1}$]GDNF appeared to have a biphasic dose response curve; efficacy decreased to about 60% of normal at both the higher 100 μg/day and lower 1 μg/day doses, while efficacy was lost at 0.1 μg/day. NGF treatment also sustained p75 expression in 90% of the axotomized neurons with similar efficacy at both 10 μg/day and 1 μg/day. BDNF treatment sustained p75 expression in 70% of the neurons at a dose of 10 μg/day, but efficacy was lost at the lower doses of 1 and 0.1 μg/day.

On histological examination, vehicle-treated animals exhibited an obvious loss of p75-positive neurons on the side ipsilateral to the axotomy (right) compared to the contralateral control (left) side. Treatment with [Met$^{-1}$] GDNF at 10 μg/day, NGF at 1 μg/day, and BDNF at 10 μg/day significantly reduced the loss of p75-positive neurons, sustaining the cholinergic phenotype in the axotomized cells. [Met$^{-1}$]GDNF-treated neurons were similar in size and appearance to normal neurons, vehicle-treated neurons, and neurons on the contralateral side. The apparent expression of p75 immunoreactivity and size of the NGF-treated neurons were generally greater than normal and vehicle-treated animals, and the effect was bilateral. NGF treatment also resulted in an apparent induction of p75-positive perineuronal sprouting on both sides of the medial septum, with a greater effect noted on the axotomized right side. The impact of BDNF on perineuronal p75 sprouts was negligible.

Figure 5:
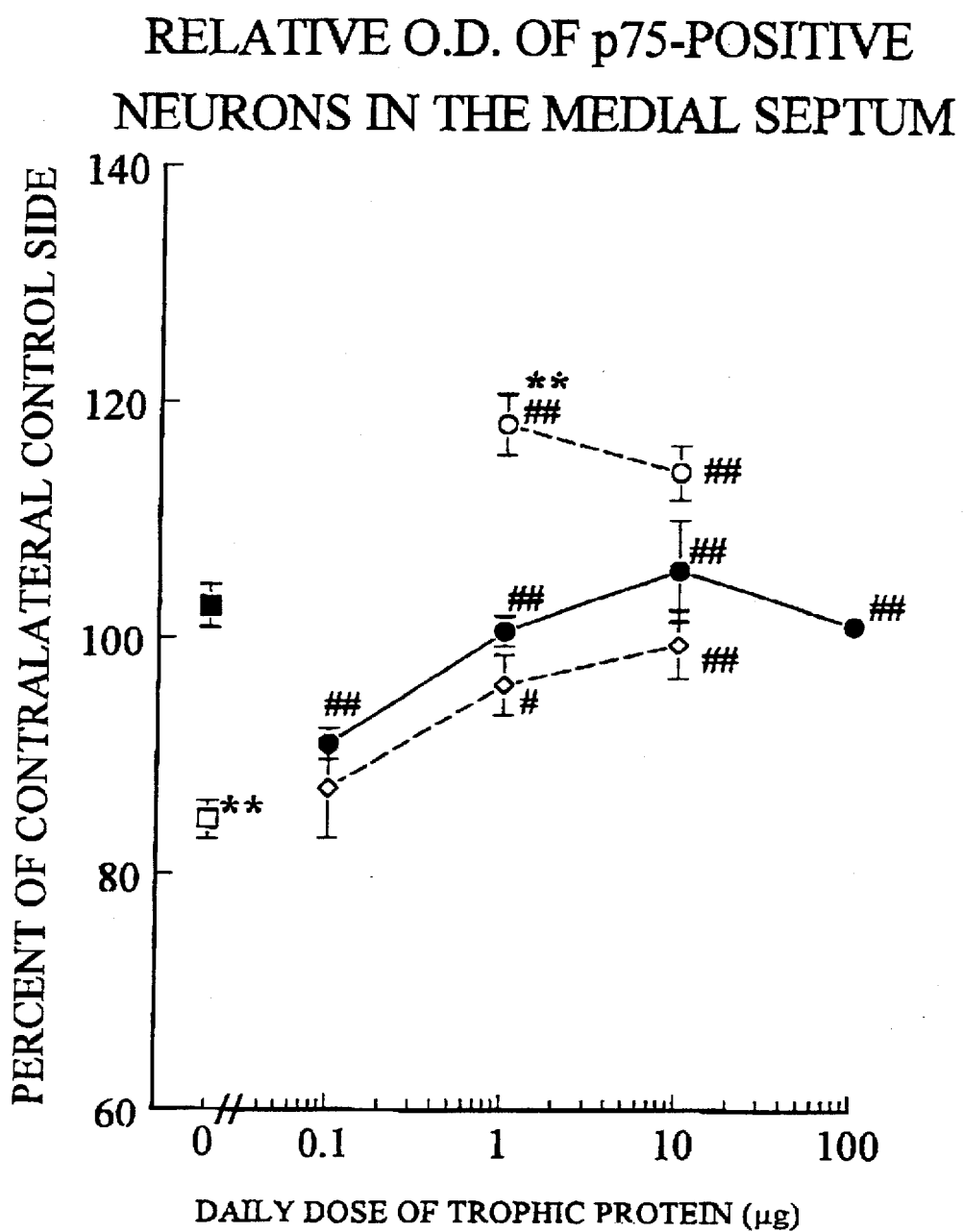
FIGS. 5 and 6 display the effect of [Met$^{-1}$]GDNF, BDNF, NGF or vehicle treatment on the relative O.D. of p75 immunoreactivity in the medial (FIG. 5) and lateral (FIG. 6) septum after fimbria/fornix axotomy.

Quantitative densitometry of the perineuronal p75 immunoreactivity in the medial septum and diagonal band provided a useful surrogate marker of the effects of axotomy and neurotrophic factor treatment. FIG. 5 displays the effects of [Met$^{-1}$]GDNF (closed circles), NGF (open circles), and BDNF (open diamonds) on the relative optical density of p75 immunoreactivity in the medial septum after axotomy (sample n=10 except for: normal, n=6; and BDNF at 0.1 μg/day, n=4). The data is expressed as the percent ratio (mean±SEM) of the optical density measured on the right side ipsilateral to the axotomy with an MCID image analysis system, compared to the contralateral control side. (The symbol (**) signifies $p<0.01$ compared to normal animals, while the symbol (#) signifies $p<0.05$ and the symbol (##) signifies $p<0.01$ compared to vehicle-treated animals.) A significant 20% loss of relative O.D. was observed on the axotomized side in vehicle-treated animals (open squares). In [Met$^{-1}$]GDNF-treated animals, the relative O.D. on the axotomized side was significantly greater than control at all doses tested, even at the lowest dose of 0.1 μg/day, and reached normal levels at a dose of 1 μg/day. As reported previously, NGF treatment augmented p75 expression to supranormal levels, i.e. to 120% of normal at a dose of 1 μg/day, significantly greater than in both vehicle-treated and normal animals. BDNF treatment also resulted in significantly greater expression of p75 than in vehicle-treated animals, but this apparent efficacy was lost at the lowest dose of 0.1 μg/day.

Figure 6:
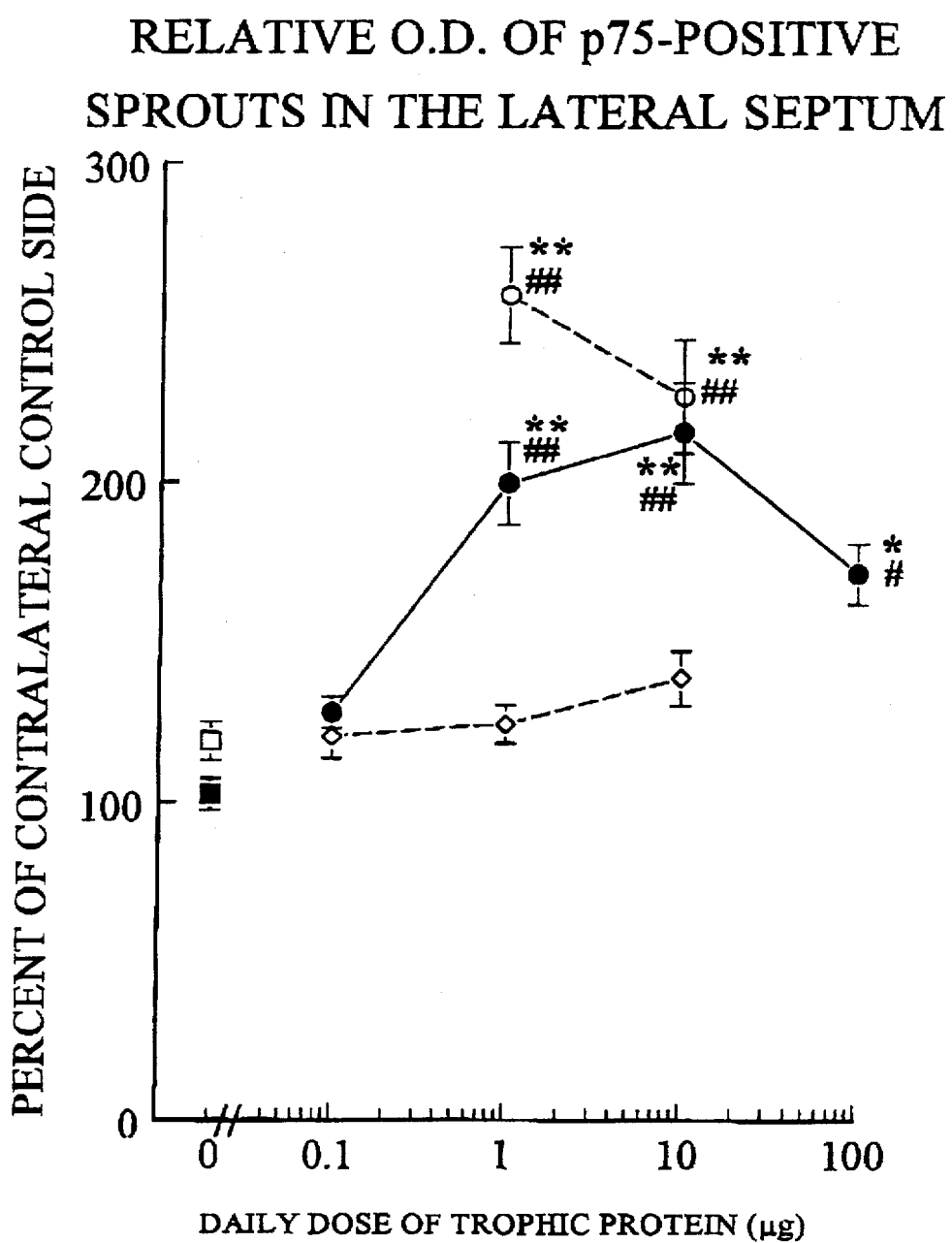

FIG. 6 shows the effects of [Met$^{-1}$]GDNF (closed circles), NGF (open circles), and BDNF (open diamonds) on the relative optical density of p75 immunoreactive sprouts in the lateral septum after axotomy (sample n=10 except for: normal, n=6; and BDNF at 0.1 μg/day, n=4). The data is expressed as the percent ratio (mean±SEM) of the optical density measured on the right side ipsilateral to the axotomy with an MCID image analysis system, compared to the contralateral control side. (The symbol (*) signifies $p<0.05$ and the symbol (**) signifies $p<0.01$ compared to normal animals, while the symbol (#) signifies $p<0.05$ and the symbol (##) signifies $p<0.01$ compared to vehicle-treated animals.) In vehicle-treated animals (open squares), there was no change in the density compared to normal animals (closed square). [Met$^{-1}$]GDNF and NGF induced a significant accumulation of p75-positive fibers that were 2- to 2.5-fold more optically dense than on the contralateral control side. The most efficacious dose of [Met$^{-1}$]GDNF was 10 μg/day. BDNF treatment resulted in an optical density only slightly larger than controls.

On histological examination, vehicle-treated animals exhibited an obvious atrophy of the lateral septum, presumably due to the loss and retrograde degeneration of the axotomized septohippocampal projection, with little or no p75 immunoreactivity in the lateral septum ipsilateral to the axotomy compared to the contralateral side. [Met$^{-1}$]GDNF treatment at 10 µg/day resulted in a large accumulation of p75 immunoreactive sprouts in the lateral septum ipsilateral to the axotomy, throughout the width of the lateral septum. Such p75-positive sprouts are not seen in normal rats, vehicle-treated rats, or on the contralateral control side. As reported previously, NGF treatment at 1 µg/day induces an even greater accumulation of acetylcholinesterase positive and p75 immunoreactive sprouts in the lateral septum ipsilateral to the axotomy, throughout the width of the lateral septum. BDNF treatment at 10 µg/day resulted in only a minor accumulation of p75 immunoreactivity limited in distribution primarily to the middle third of the lateral septum. Although neurotrophic factor treatment sustained the cholinergic phenotype of the axotomized neurons and induced the accumulation of sprouts in the lateral septum, the atrophy of the lateral septum was not affected. Quantitative measurements of the area of the lateral septum indicated that there was no effect of neurotrophic factor treatment on the area of the lateral septum ipsilateral to the axotomy, i.e., the area of the lateral septum was significantly less than normal in all treatment groups.

Figure 7:
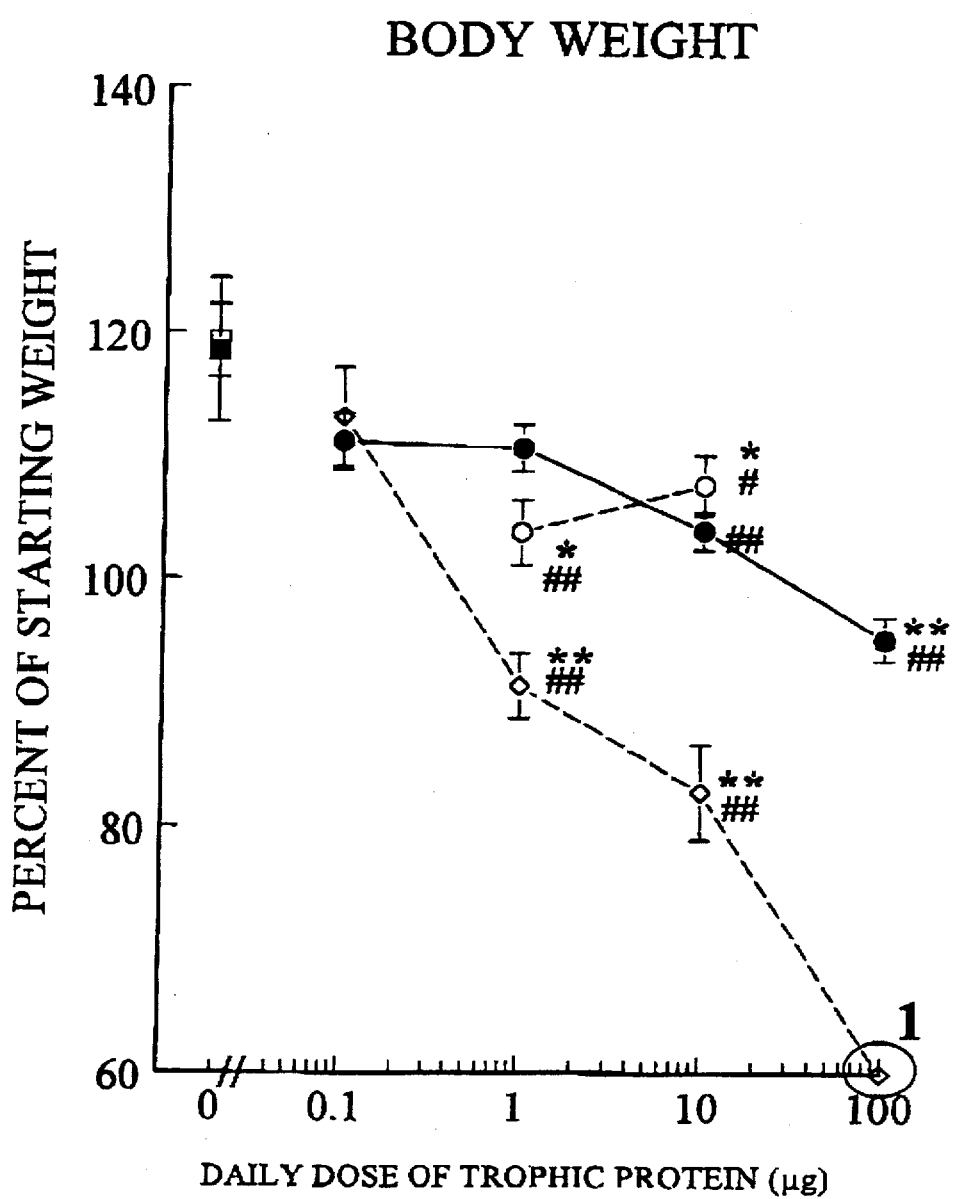
FIG. 7 displays the effect of [Met$^{-1}$]GDNF, BDNF, NGF or vehicle treatment on body weight after fimbria/fornix axotomy.

FIG. 7 displays the effect of [Met$^{-1}$]GDNF (closed circles), NGF (open circles), and BDNF (open diamonds) on animal body weight (sample n=10 except for: normal, n=6; and BDNF at 0.1 µg/day, n=4). The data is expressed as the percent (mean±SEM) of the ending body weight after two weeks of neurotrophic factor treatment compared to the starting body weight. (Symbols: (*) signifies p<0.05 and (**) signifies p<0.01 compared to normal animals, while (#) signifies p<0.05 and (##) signifies p<0.01 compared to vehicle-treated animals). Both normal (closed squares) and vehicle-treated animals (open squares) gained 20% of their starting weight. [Met$^{-1}$]GDNF at 100 and 10 µg/day, but not at 1 µg/day, inhibited this weight gain. As reported previously, NGF inhibited weight gain at both 10 µg/day and 1 µg/day doses. However, BDNF induced a significant weight loss; in fact, animals treated with BDNF at 100 µg/day (n=6) died within the first seven days of treatment.

The results of these experiments indicate that basal forebrain cholinergic neurons are another distinct neuronal population of the CNS that is responsive to GDNF protein product, in addition to mesencephalic dopaminergic and somatic motor neurons. Infusion of exogenous GDNF protein product at doses from 1 µg/day to 100 µg/day has a positive effect on axotomized basal forebrain neurons by sustaining their expression of p75 and ChAT receptors significantly above the level observed after vehicle infusion, enabling a regenerative response of axonal growth into the lateral septum, and enhancing ChAT enzyme activity in an axotomy-dependent manner to levels greater than those found in normal animals. Although it is similar in efficacy to NGF and BDNF, GDNF protein product induces a unique phenotype in treated, axotomized animals. The efficacy of GDNF protein product on sustaining dystrophic basal forebrain cholinergic neurons demonstrates that it is a potentially useful therapeutic for cholinergic degenerative diseases such as Alzheimer's disease, and the unique properties of GDNF protein product may offer advantages for such therapy over other neurotrophins.

In the present experiments, GDNF protein product and NGF exhibited similar efficacy in sustaining essentially 100% of the number of axotomized p75-positive neurons and similar efficacy in inducing p75 immunoreactive sprouts in the lateral septum. However, the potency of NGF is at least an order of magnitude higher than GDNF protein product. An NGF dose of 1 µg/day sustained expression of p75 immunoreactivity in 100% of the neurons, while a GDNF protein product dose of 10 µg/day was required to achieve the same effect. GDNF protein product also sustained fewer (60%) ChAT-positive neurons than NGF (90%).

Although GDNF protein product neurotrophic efficacy was similar to that of BDNF with respect to sustaining ChAT- and p75-positive neurons, GDNF protein product was an order of magnitude more potent than BDNF and had efficacies clearly separable from BDNF in its induction of p75 immunoreactive sprouting into the lateral septum and its effects on weight gain. The effective doses of GDNF protein product in the fimbria/fornix axotomy model are comparable to those reported for the in vivo efficacy of GDNF on mesencephalic dopaminergic neurons (Hoffer et al., *Neurosci. Lett.* 182:107–111, 1994; Hudson et al., *Brian Res. Bull.* 36:425–432, 1995; Kearns and Gash, *Brain Res.* 672:104–111, 1995; Strumberg et al., *Exp. Neurol.* 124:401–412, 1995).

In the present experiments, NGF stimulated to supranormal levels ChAT biochemical activity and ChAT and p75 immunoreactivity in presumptively normal uninjured neurons. An axotomy-dependent induction of super-sensitivity to NGF was also observed such that ChAT enzyme activity was stimulated to even greater levels in the injured septum (70% greater than observed in the contralateral, uninjured septum). GDNF protein product stimulated ChAT biochemical activity only in axotomized neurons, not in normal neurons. BDNF, on the other hand, had no stimulatory effect on ChAT biochemical activity either in axotomized or uninjured neurons.

The efficacy of GDNF protein product on the axotomized cholinergic neurons is presumably a receptor-mediated phenomenon. Although GDNF protein product treatment was not observed to have any effect on the contralateral control side or in non-axotomized normal animals infused with GDNF protein product at 10 µg/day, axotomy of the fimbria/fornix clearly induces a sensitivity of the basal forebrain cholinergic neurons to exogenous GDNF and treatment with GDNF protein product prevents the loss, i.e., sustains the expression, of both p75 and ChAT phenotypes. This may suggest that normal basal forebrain neurons do not express physiologically relevant levels of GDNF receptor, and that the axotomy-induced sensitivity to GDNF protein product may be a result of an axotomy-induced up-regulation or activation of the GDNF receptor.

These results show that the effects of GDNF protein product on dystrophic cholinergic neurons are more modest than the effects of NGF, and that GDNF protein product, unlike NGF, has minimal or no effect on uninjured normal neurons. In initial safety studies, GDNF protein product was very well tolerated in rats after systemic administration and showed no adverse side affects such as hyperalgesia or weight loss even at high doses. Although BDNF has similar efficacy as GDNF protein product, it is an order of magnitude less potent than GDNF protein product, does not affect ChAT biochemical activity, and induces severe weight loss.

EXAMPLE 3

GDNF protein product is further tested for its ability to improve cognitive function in animal models of age-related dementia according to Fischer et al., *Proc. Nat'l. Acad. Sci. USA*, 91:8607–8611, 1994. Briefly, aged female rats (22–24 months old) are selected for impairments in spatial learning and memory (often associated with marked cellular atrophy of forebrain cholinergic neurons) in the Morris water maze task. Controls are young female rats (3 months old). Each rat is given an intracerebroventricular infusion of GDNF protein product or vehicle for four weeks, during which time the rat's performance in the water maze is tested periodically to evaluate its acquisition and retention of spatial memory. GDNF protein product is also evaluated in other Alzheimer disease models, e.g., rats that develop cerebral amyloidosis.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

We claim:

1. A method for treating injury or degeneration of basal forebrain cholinergic neurons comprising administering to a subject suffering from such injury or degeneration a therapeutically effective amount of a glial cell line-derived neurotrophic factor (GDNF) protein product.

2. The method of claim 1 wherein the injury or degeneration of basal forebrain cholinergic neurons is associated with Alzheimer's disease.

3. The method of claim 1 wherein the GDNF protein product is the amino acid sequence set forth in SEQ ID NO: 1 or a variant, or a derivative thereof.

4. The method of claim 3 wherein the GDNF protein product has the amino acid sequence set forth in SEQ ID NO: 1.

5. The method of claim 3 wherein the GDNF protein product is [Met$^{-1}$]GDNF.

6. The method of claim 3 wherein the GDNF protein product comprises a water soluble polymer.

7. The method of claim 6 wherein the water soluble polymer is polyethylene glycol.

8. The method of claim 1 wherein the GDNF protein product is administered at a dose between about 10 µg/kg/day and 100 mg/kg/day.

9. The method of claim 1 wherein the GDNF protein product is administered at a dose between about 1 mg/kg/day and 25 mg/kg/day.

10. The method of claim 2 further comprising administering to the patient an effective amount of a second therapeutic agent for Alzheimer's disease.

11. The method of claim 10 wherein the second therapeutic agent is selected from the group consisting of cholinesterase inhibitors, nerve growth factor (NGF), brain derived neurotrophic factor (BDNF), neurotrophin-3 (NT-3), neurotrophin-4/5 (NT-4/5), basic fibroblast growth factor (bFGF), and ciliary neurotrophic factor (CNTF).

* * * * *

UNITED STATES PATENT AND TRADEMARK OFFICE
CERTIFICATE OF CORRECTION

PATENT NO.  : 5,731,284
DATED       : March 24, 1998
INVENTOR    : Lawrence R. Williams It is certified that error appears in the above-identified patent and that said Letters Patent is hereby corrected as shown below:

Cover Page [54], Line 2, add --CELL-- after GLIAL.

Column 1, Line 2, add --CELL-- after GLIAL.

Column 3, Line 62, change 'CHAT" to --ChAT--.

Column 4, Line 18, change "Heft" to --Hefti--.

Column 5, Line 32, change "mount" to --amount--.

Column 7, Line 4, change "conical" to --cortical--.

Column 13, Line 43, change "("NITS")" to --("NHS")--.

Column 19, Line 43, change "confined" to --confirmed--.

Signed and Sealed this

Twenty-sixth Day of May, 1998

BRUCE LEHMAN

Attest:

Attesting Officer

Commissioner of Patents and Trademarks

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 134 amino acid residues
( B ) TYPE: amino acid
( D ) TOPOLOGY: linear ( i x ) FEATURE:
( A ) NAME/KEY: inferred amino acid sequence for mature human GDNF ( x i ) SEQUENCE DESCRIPTION: SEQ ID NO:1:

```
Ser Pro Asp Lys Gln Met Ala Val Leu Pro Arg Arg Glu Arg Asn Arg
 1               5                  10                      15
Gln Ala Ala Ala Ala Asn Pro Glu Asn Ser Arg Gly Lys Gly Arg Arg
             20                  25                  30
Gly Gln Arg Gly Lys Asn Arg Gly Cys Val Leu Thr Ala Ile His Leu
         35                  40                  45
Asn Val Thr Asp Leu Gly Leu Gly Tyr Glu Thr Lys Glu Glu Leu Ile
     50                  55                  60
Phe Arg Tyr Cys Ser Gly Ser Cys Asp Ala Ala Glu Thr Thr Tyr Asp
 65                  70                  75                  80
Lys Ile Leu Lys Asn Leu Ser Arg Asn Arg Arg Leu Val Ser Asp Lys
                 85                  90                  95
Val Gly Gln Ala Cys Cys Arg Pro Ile Ala Phe Asp Asp Leu Ser
             100                 105                 110
Phe Leu Asp Asp Asn Leu Val Tyr His Ile Leu Arg Lys His Ser Ala
         115                 120                 125
Lys Arg Cys Gly Cys Ile
         130
```